(12) United States Patent
Stack et al.

(10) Patent No.: US 7,431,725 B2
(45) Date of Patent: Oct. 7, 2008

(54) DEVICES AND METHODS FOR RETAINING A GASTRO-ESOPHAGEAL IMPLANT

(75) Inventors: Richard S. Stack, Chapel Hill, NC (US); Dan Balbierz, Redwood City, CA (US); John Lunsford, San Carlos, CA (US); Kevin van Bladel, Livermore, CA (US); William S. Eubanks, Jr., Columbia, MO (US); William L. Athas, Chapel Hill, NC (US); Richard A. Glenn, Santa Rosa, CA (US); Richard Kouri, Raleigh, NC (US)

(73) Assignee: Synecor, LLC, Durham, NC (US)

( * ) Notice: Subject to any disclaimer, the term of this patent is extended or adjusted under 35 U.S.C. 154(b) by 260 days.

(21) Appl. No.: 10/898,036

(22) Filed: Jul. 23, 2004

(65) Prior Publication Data

US 2005/0096673 A1  May 5, 2005

Related U.S. Application Data

(63) Continuation-in-part of application No. 10/843,702, filed on May 11, 2004.

(60) Provisional application No. 60/510,268, filed on Oct. 10, 2003.

(51) Int. Cl.
*A61B 17/08* (2006.01)
*A61B 17/10* (2006.01)

(52) U.S. Cl. ..................... 606/151; 606/139
(58) Field of Classification Search ................ 606/142, 606/144, 151, 153, 154, 139, 155
See application file for complete search history.

(56) References Cited

U.S. PATENT DOCUMENTS 6,994,715 B2 *   2/2006  Gannoe et al. ............. 606/153
2004/0092892 A1 *  5/2004  Kagan et al. ............... 604/264

* cited by examiner

*Primary Examiner*—Todd E. Manahan
*Assistant Examiner*—Timothy J Neal
(74) *Attorney, Agent, or Firm*—Stallman & Pollock LLP

(57) ABSTRACT

Various methods and devices are described for retaining a medical implant within a body cavity. According to one aspect, one or more plications are formed and the medical device is coupled to or seated against the plication(s). A patch may be positioned between tissue layers forming the plication so as to reinforce the tissue adhesion forming between the tissue layers.

16 Claims, 39 Drawing Sheets

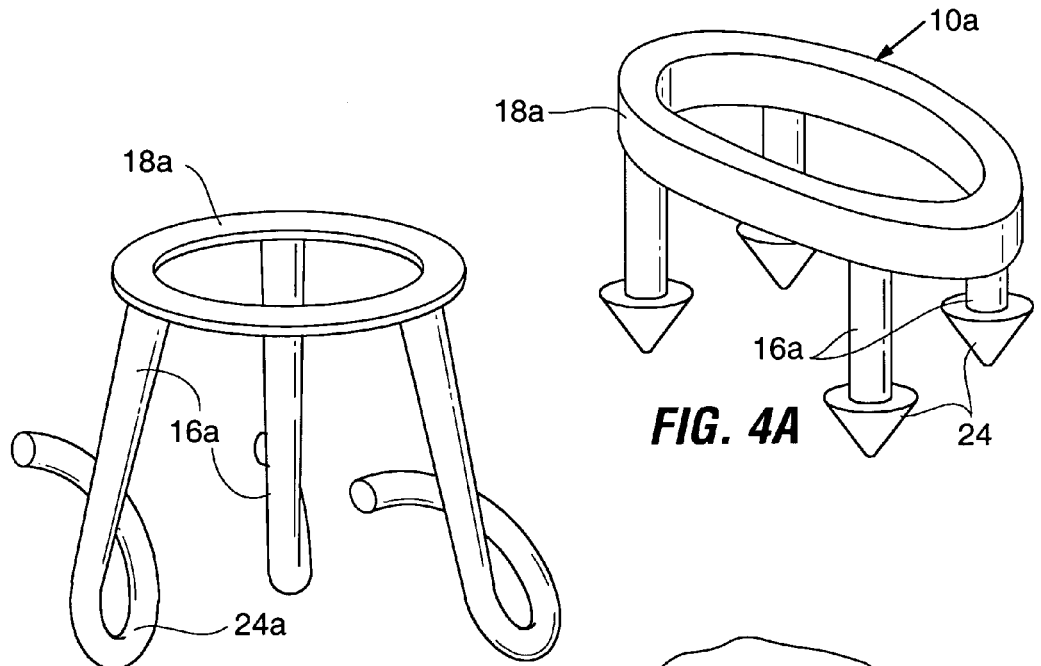
FIG. 4A
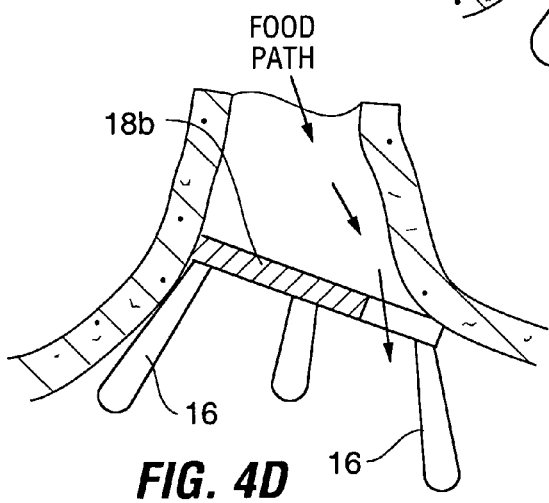
FIG. 4B
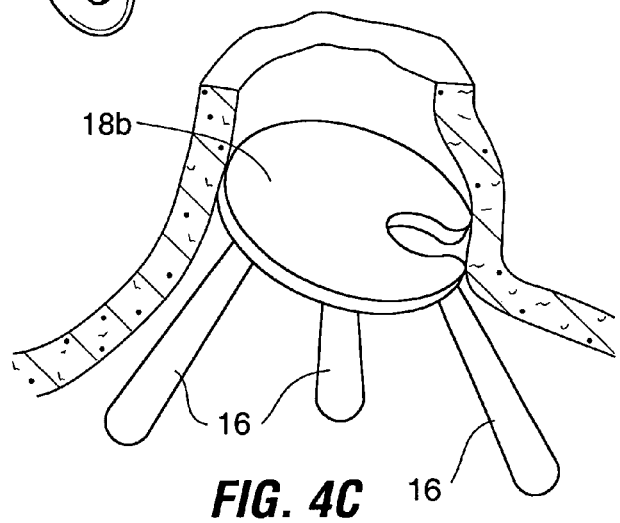
FIG. 4C
FIG. 4D

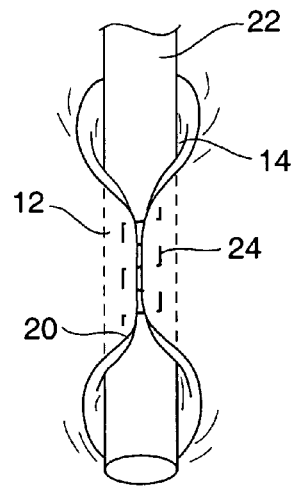
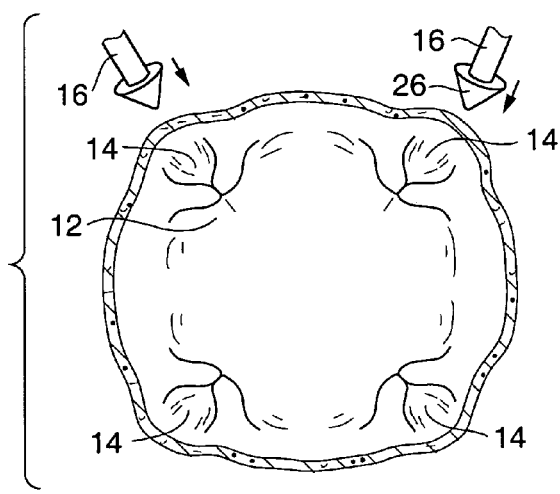
FIG. 5A  FIG. 5B
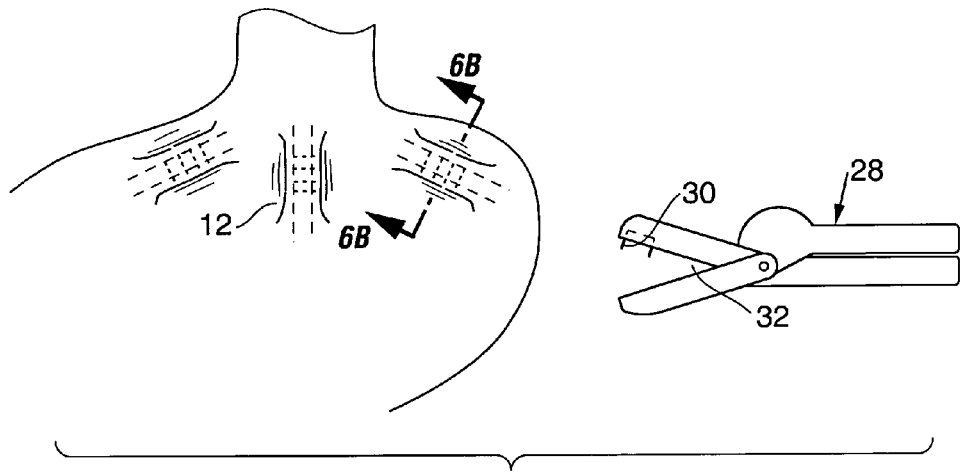
FIG. 6A
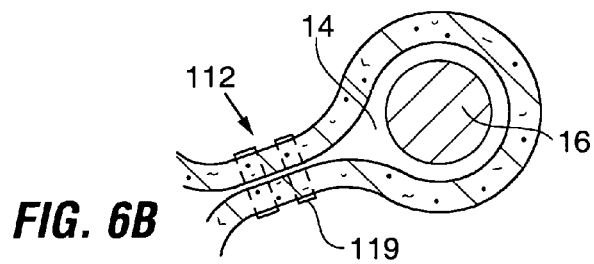
FIG. 6B

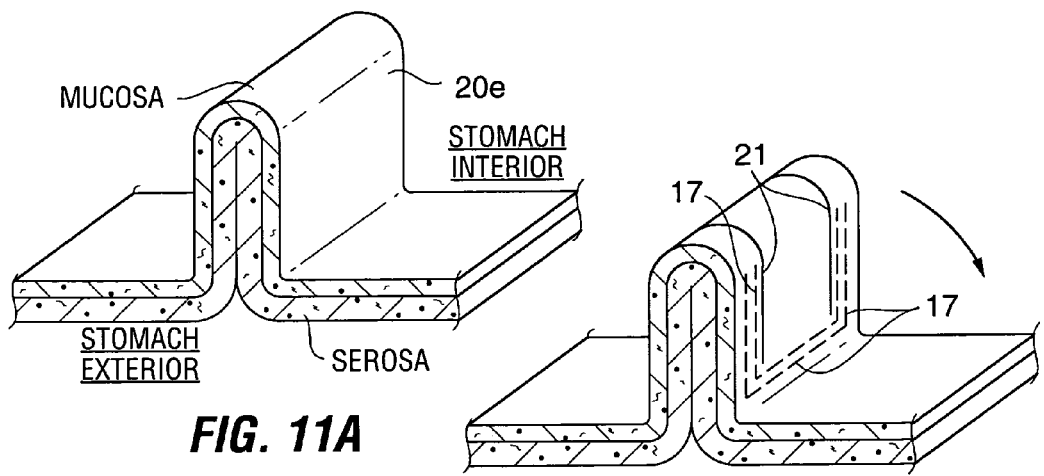
FIG. 11A
FIG. 11B
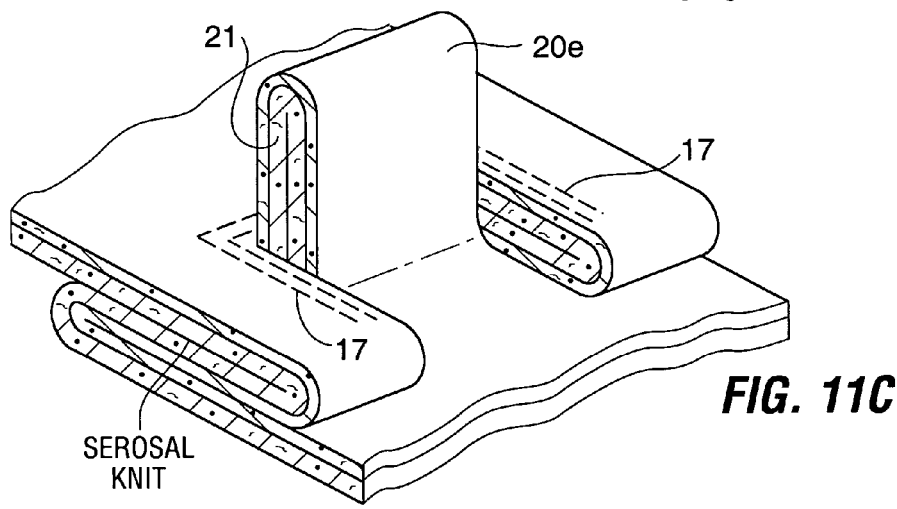
FIG. 11C
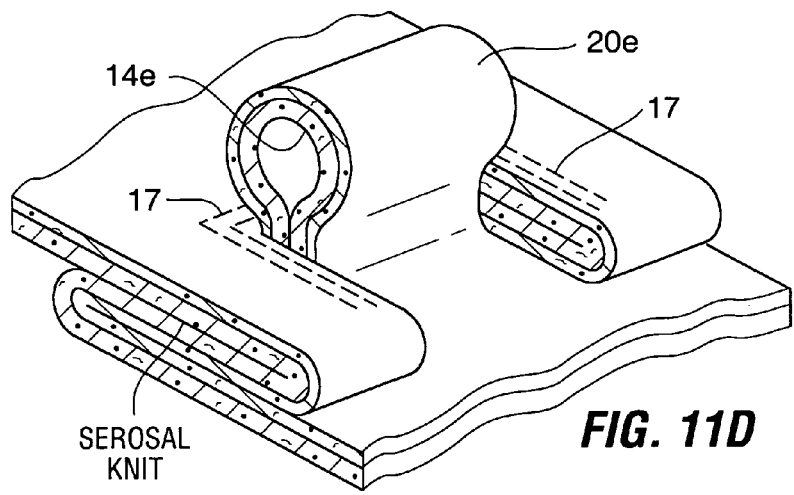
FIG. 11D

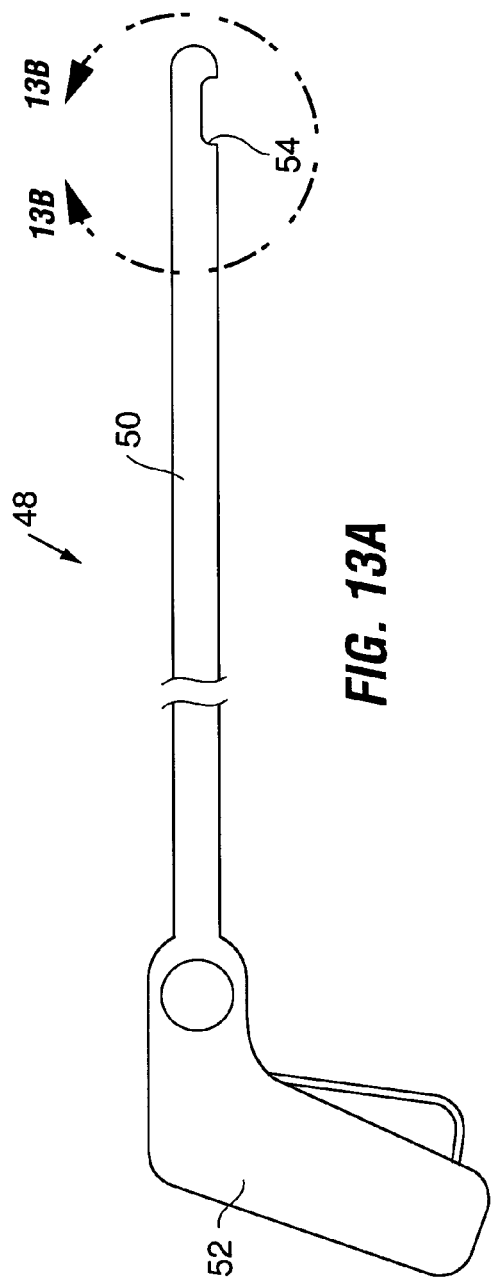
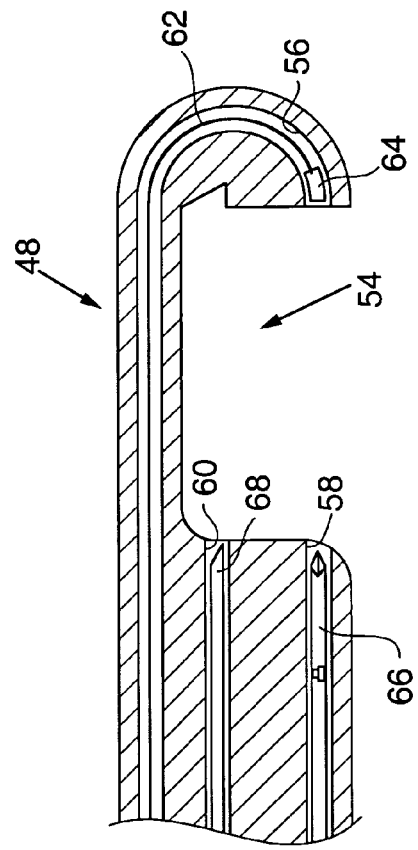

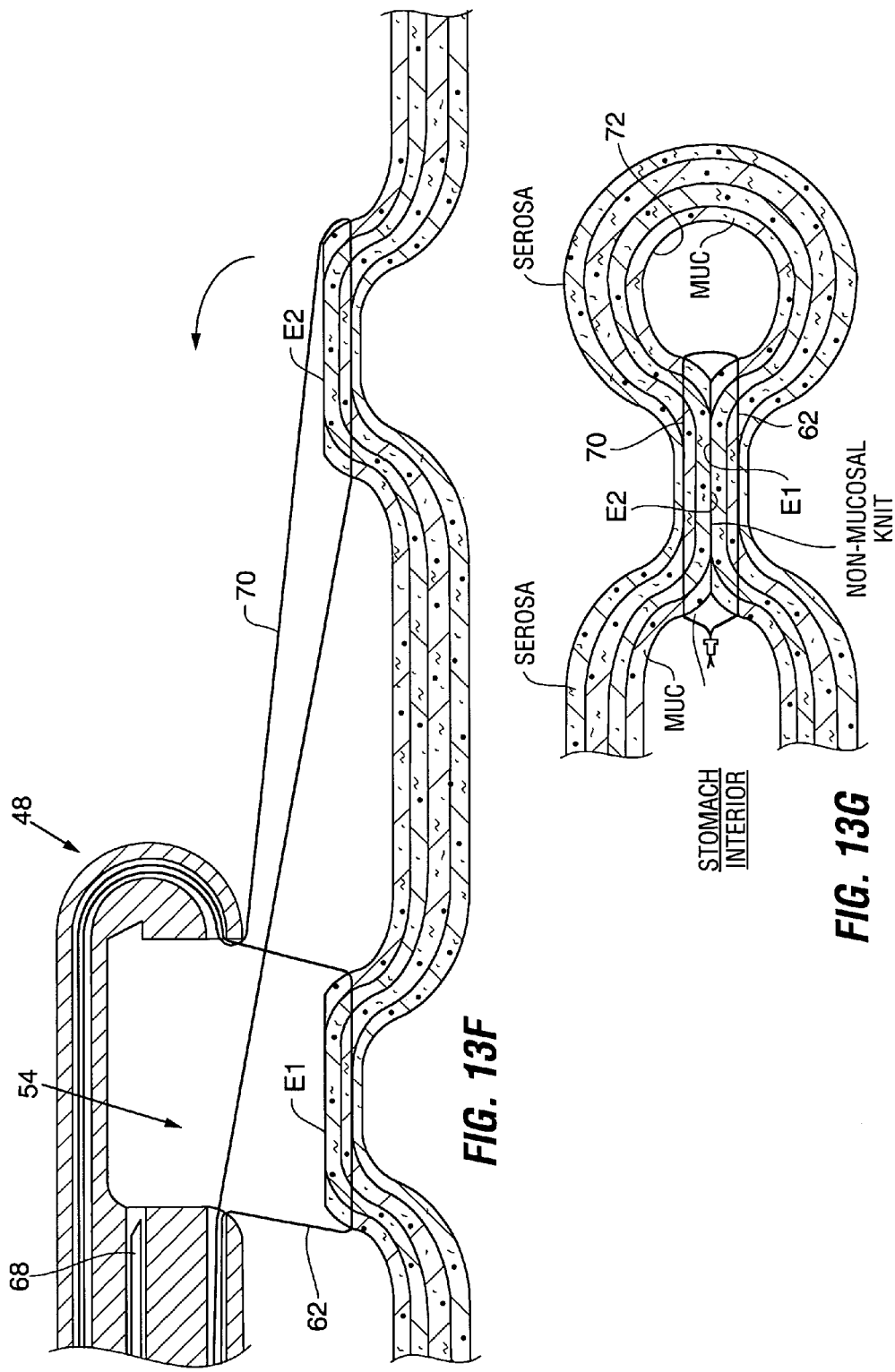

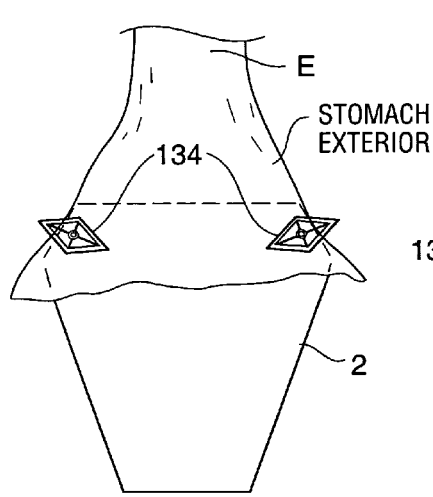
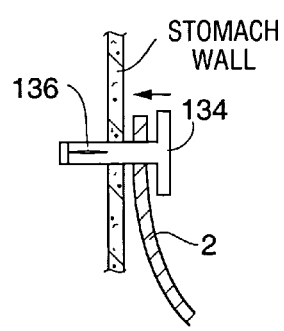
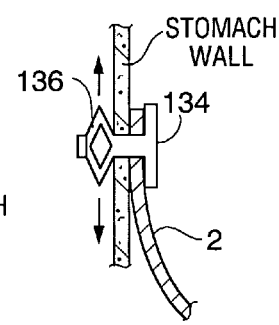
FIG. 27A  FIG. 27B  FIG. 27C
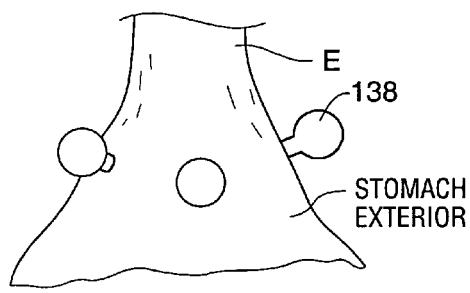
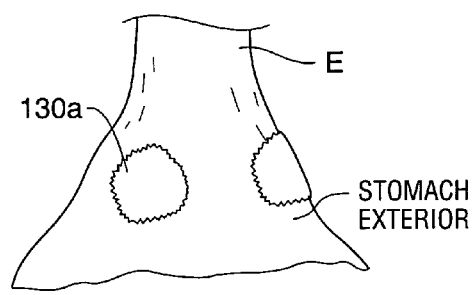
FIG. 28A  FIG. 28B
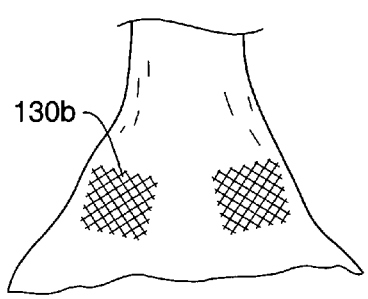
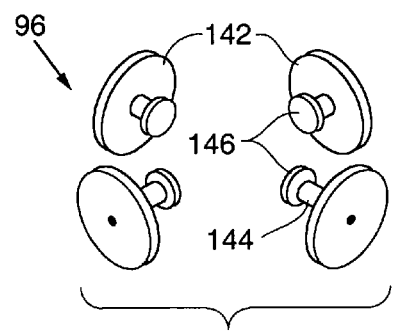
FIG. 28C  FIG. 29A

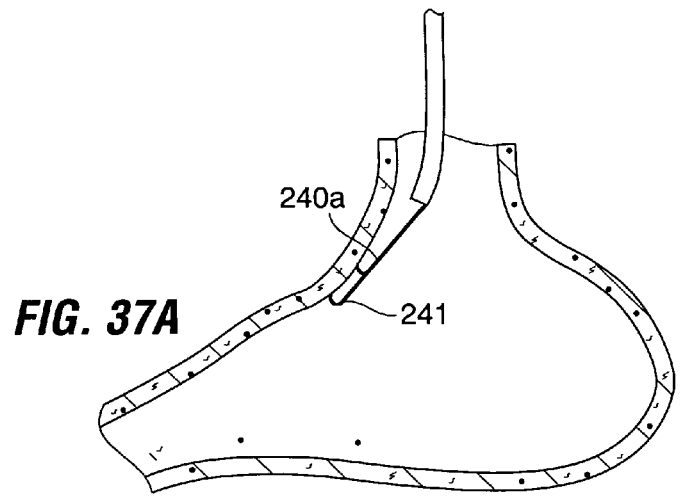
FIG. 37A
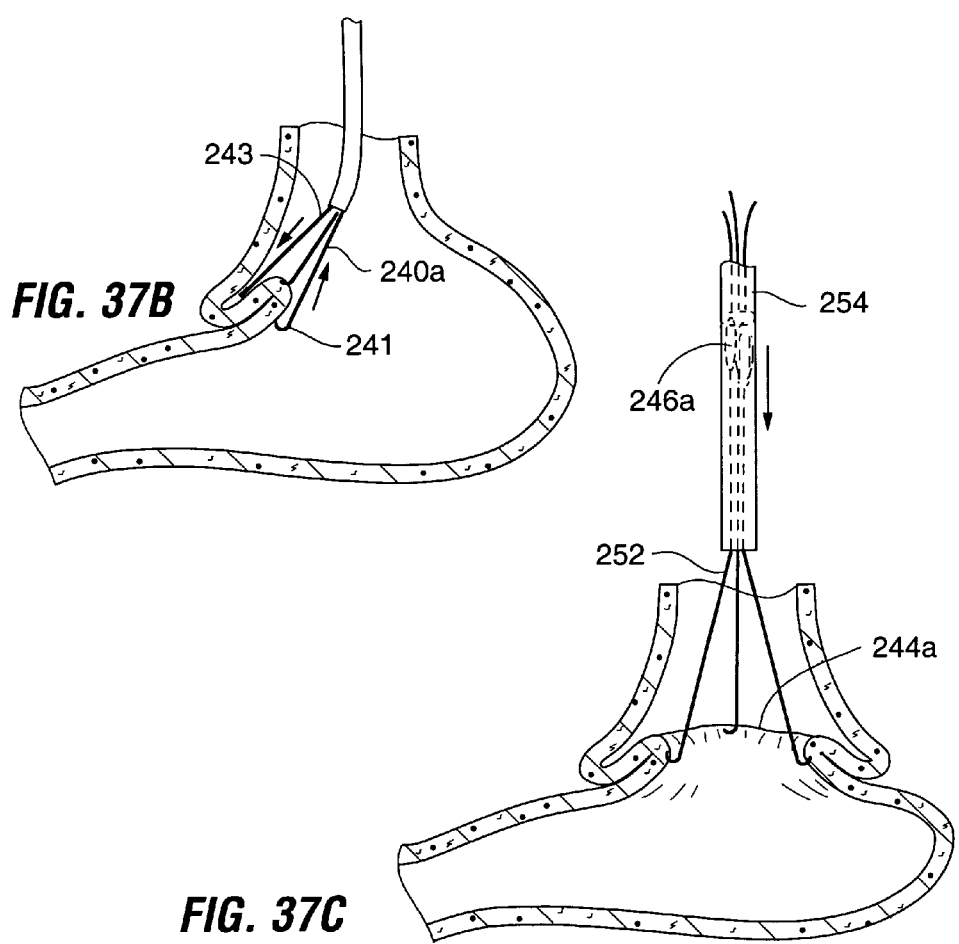
FIG. 37B
FIG. 37C

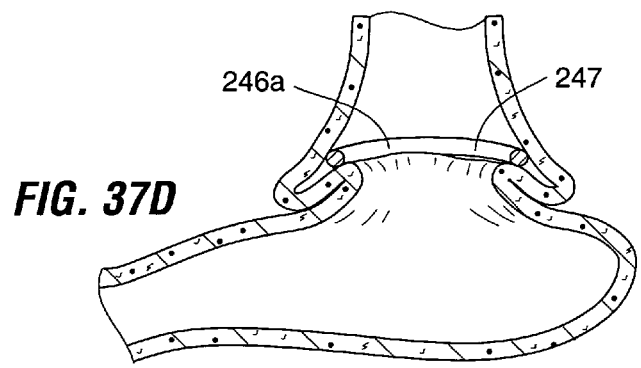
FIG. 37D
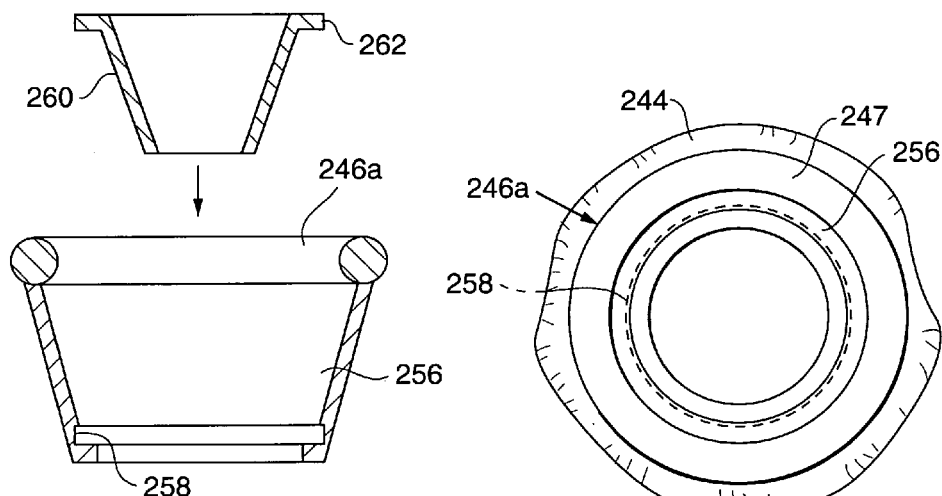
FIG. 37E
FIG. 37F
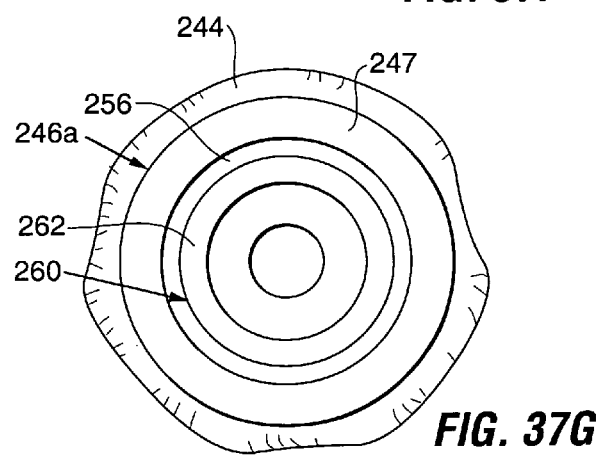
FIG. 37G

SEROSA — MUCOSA

US 7,431,725 B2

DEVICES AND METHODS FOR RETAINING A GASTRO-ESOPHAGEAL IMPLANT

This application is a continuation in part of U.S. patent application Ser. No. 10/843,702, filed May 11, 2004 and claims the benefit of U.S. Provisional Application No. 60/510,268, filed Oct. 10, 2003.

FIELD OF THE INVENTION

The present invention relates generally to the field of gastro-esophageal implant devices, and specifically to devices and methods for retaining such implants within the gastro-esophageal junction region or stomach of a patient.

BACKGROUND OF THE INVENTION

An anatomical view of a human stomach S and associated features is shown in FIG. 1A. The esophagus E delivers food from the mouth to the proximal portion of the stomach S. The z-line or gastro-esophageal junction Z is the irregularly-shaped border between the thin tissue of the esophagus and the thicker tissue of the stomach wall. The gastro-esophageal junction region G is the region encompassing the distal portion of the esophagus E, the z-line, and the proximal portion of the stomach S.

Stomach S includes a fundus F at its proximal end and an antrum A at its distal end. Antrum A feeds into the pylorus P which attaches to the duodenum D, the proximal region of the small intestine. Within the pylorus P is a sphincter that prevents backflow of food from the duodenum D into the stomach. The middle region of the small intestine, positioned distally of the duodenum D, is the jejunum J.

FIG. 1B illustrates the tissue layers forming the stomach wall. The outermost layer is the serosal layer or "serosa" S and the innermost layer, lining the stomach interior, is the mucosal layer or "mucosa" MUC. The submucosa SM and the multi-layer muscularis M lie between the mucosa and the serosa.

Various types of implants are positionable within the esophagus or stomach. These include prosthetic valves implanted for treatment of gastro-esophageal reflux disease. Another category of stomach implants includes prosthetic implants for controlling obesity. These include space-occupying devices such as inflatable balloons tethered to the stomach interior. Other obesity-controlling implants are shown and described in U.S. application Ser. No. 09/940,110, filed Aug. 27, 2001 and U.S. application Ser. No. 10/118,211006 filed Apr. 8, 2002, and U.S. Provisional Application No. 60/379,306 filed May 10, 2002, U.S. application Ser. Nos. 10/345,666 and 10/345,1104 filed Jan. 16, 2003. These applications are owned by the assignee of the present application, and the disclosures of these applications are incorporated herein by reference. Certain forms of these devices involve positioning a restrictive device in the proximal stomach. For example, a prosthetic pouch 2 of the type shown in FIG. 2A may be positioned in the proximal stomach or at the gastro-esophageal junction region as shown in FIG. 2B. The pouch may act as a restrictor, limiting the amount of food intake by restricting passage of food from the esophagus into the stomach.

This type of pouch 2 may include a proximal opening 4 and a smaller distal opening 6 and forms a small reservoir that collects masticated food from the esophagus—thereby limiting the amount of food that can be consumed at one time. Because of its small volume (which may be on the order of approximately 2 cc-300 cc in volume, but is preferably in the range of 10-30 cc), the pouch functions to limit the amount of food that can be consumed at one time. Over time the food within this reservoir descends into the stomach through the distal opening.

As the pouch fills with food, it may distend, imparting pressure against the upper stomach and lower esophageal sphincter causing the patient to experience sensations of fullness. Other types of restrictive devices are disclosed in the above-identified prior applications as well as in this application.

The pouch 2 or other restrictive implant may be formed of a flexible material. Examples of such materials include, but are not limited to polyesters (e.g. Dacron® polyester), ePTFE fabric (e.g. GoreTex® fabric or others), a polyurethane such as ChronoFlex® polyurethane, nylon fabrics, silicone, other polymeric materials, and bio-absorbable materials (e.g. PLLA, PGA, PCL, poly-amhydride etc). In the case of the pouch 2, it is optimal but not mandatory that the material prevents passage of food through the sides of the pouch. The material may be a composite of compliant, semi-compliant and/or non-compliant materials that give different regions of the pouch different degrees of compliance so as to allow/limit expansion of the pouch in various locations. For example, it may be desirable to provide a pouch with a fairly elastic exit port to as to prevent occlusion in the event a large piece of food is ingested and/or to control the exit pressure of food from the pouch, whereas the proximal end of the pouch may be stiffer to prevent bulging. Varying degrees of compliance may also be built into the pouch by varying the cross-sectional thickness in different regions of the pouch. The material may be coated with a lubricious, bio-compatible, chemically inert material, such as paraleyne, to reduce friction on the base material's surface which will help prevent sticking and food build up on the device.

The restrictive implant may be reinforced with, constructed of, or supported by supporting members, such as a soft mesh, a cage structure, ribs, rings etc. The supporting members may be formed of stainless steel, polymer, shape memory materials such as nitinol, shape memory alloys, or shape memory polymers, or thickened regions of material. The implant may be constructed so as to be self-expanding, so that it will spring radially open into an expanded condition upon ejection from a deployment device or catheter.

The pouch 2 or other implant in the stomach/esophagus may be fixed in place using sutures 8a, 8b or other means such as clips or suitable adhesives at anchor points around the perimeter of the proximal opening 4. The implant may include a reinforced section such as rim section 9 on pouch 2 for receiving the sutures 8a, 8b or other anchoring means. As illustrated in FIG. 2B, where anchoring means such as clips or sutures are used, the anchoring means may be passed completely through the wall of the stomach as with suture 8a (called a "full thickness" suture or clip), or partially through the wall of the stomach as with suture 8b (called a "partial thickness" suture or clip). One suture attachment device found useful for applying sutures between the pouch and tissue is the "Sew-Right" suturing device available from LSI Solutions of Victor, N.Y. Although the pouch may be secured to the esophageal tissue, it is more preferable to apply sutures/clips below the Z-line to allow for attachment to the thicker tissue of the stomach wall.

Once secured within the stomach, the implant and associated anchoring means are subjected to significant forces caused by stomach motility and by forces imparted against the pouch by ingested food. Such forces may be imparted against restrictive devices such as pouch 2 as well as other forms of gastro-esophageal implants, such as prosthetic valves implanted within the esophagus for treatment of gastro-esophageal reflux disease or space-occupying implants for hunger control. Over time, such forces could cause the implant to become detached from the wall of the stomach or esophagus due to erosion of the stomach/esophageal tissue at the anchoring points. It is thus desirable to provide an anchoring mechanism that will retain an implant within the stomach and/or esophagus over an extended period of time.

SUMMARY

Various methods and devices are described for retaining a medical implant within a body cavity. According to one aspect, one or more plications are formed and the medical device is coupled to or seated against the plication(s). A patch may be positioned between tissue layers forming the plication so as to reinforce the tissue adhesion forming between the tissue layers.

BRIEF DESCRIPTION OF THE DRAWINGS

FIGS. 4A and 4B are perspective views of alternate embodiments of restrictive implant utilizing a ring as a restrictive element.

FIG. 4C is a perspective view illustrating an alternate embodiment of a restrictive implant utilizing a notched disk as a restrictive element. The implant is shown positioned at the gastro-esophageal junction region. FIG. 4D is a cross-sectional front view showing the implant positioned within the gastro-esophageal junction region.

FIG. 5A is a front perspective view of a stomach wall illustrating formation of a vertical tissue pocket formed using plications in the wall.

FIG. 5B is a perspective view looking downwardly into the interior of a stomach, illustrating placement of the implant of FIG. 4A into pockets formed by plications of the type shown in FIG. 5A.

FIG. 6A is a front schematic illustration of an esophagus and stomach, illustrating formation of tissue pockets using a surgical stapler.

FIG. 6B is a cross-section view of a tissue pocket, taken along the plane designated 6B-6B in FIG. 6A.

FIGS. 11A through 11D are a sequence of cross-sectional perspective views of a portion of stomach wall, showing yet another plication method for forming tissue pockets.

FIG. 13A is a side elevation view of suturing device for modifying a tissue surface and for forming a plication in tissue. FIG. 13B is a cross-section view of the distal portion of the device of FIG. 13A. FIGS. 13C-13G illustrate use of the device of FIGS. 13A-13B to form tissue pockets.

FIG. 27A is a schematic illustration of the exterior of a lower esophagus and proximal stomach, showing "moly bolt" type external reinforcements used to facilitate anchoring of an internally positioned restrictive device. FIGS. 27B and 27C are cross-sectional side views showing introduction of the external reinforcement device through the stomach wall and its subsequent expansion to anchor a restrictive device in place FIGS. 28A through 28C are schematic illustrations of the exteriors of a lower esophagus and proximal stomach, each showing four additional embodiments of external reinforcements used to facilitate anchoring of an internally positioned restrictive device.

FIG. 29A is a perspective view of a stud-type fastener which may be used to connect an internally positioned restrictive device to an external reinforcement device.

FIG. 30A shows the reinforcements in an equilibrium state, whereas FIG. 30B shows the alteration of the reinforcements in response to a force.

FIGS. 37A through 37D are a sequence of cross-section views illustrating a modification to the method shown in FIGS. 36A through 36F. FIG. 37E illustrates insertion of a restrictive insert into the support ring. FIGS. 37F and 37G show the support ring before and after insertion of the orifice, respectively.

DETAILED DESCRIPTION OF THE DRAWINGS

Figure 1A:
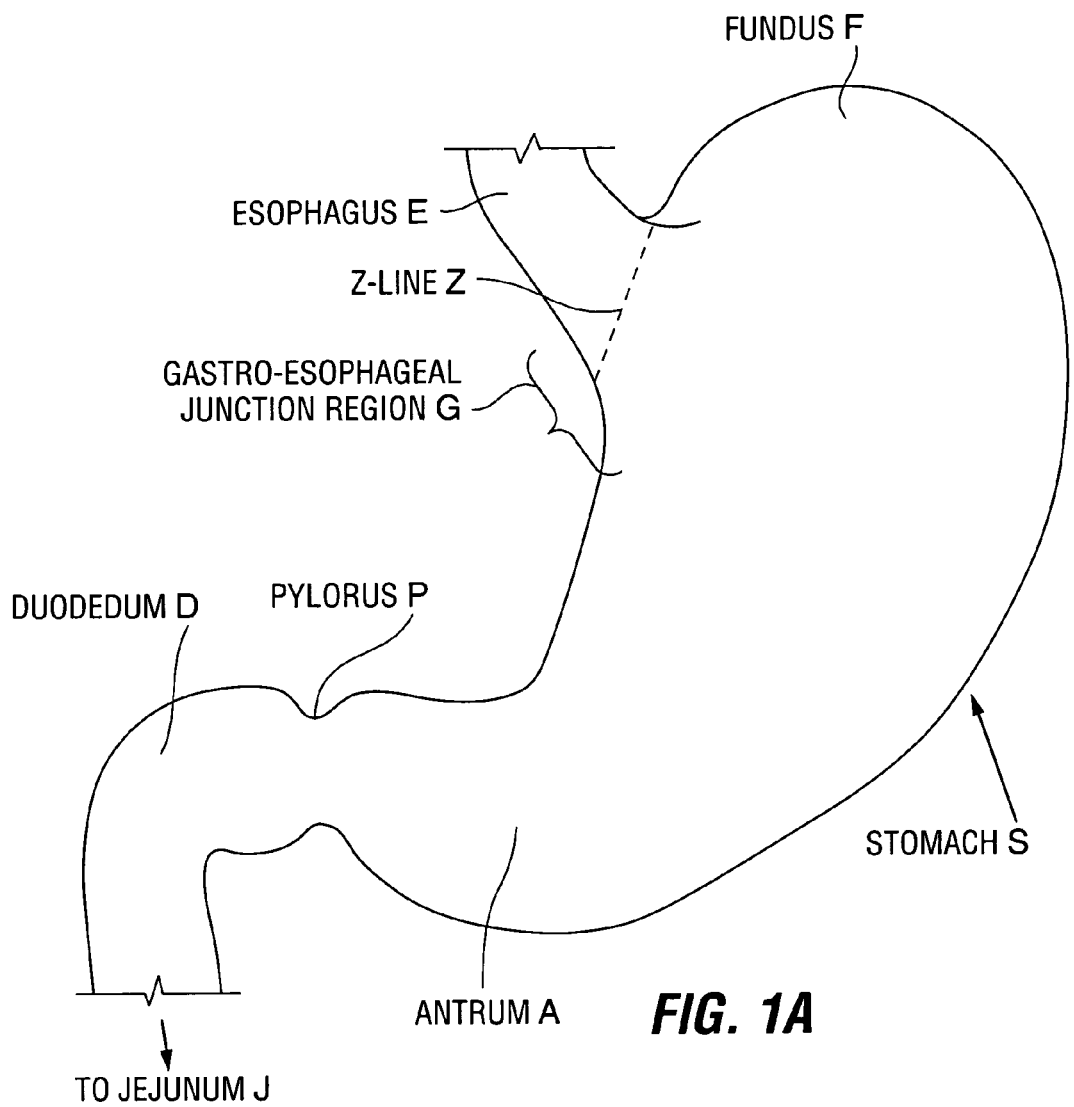
FIG. 1A is a schematic illustration of a human stomach and a portion of the small intestine.
Figure 1B:
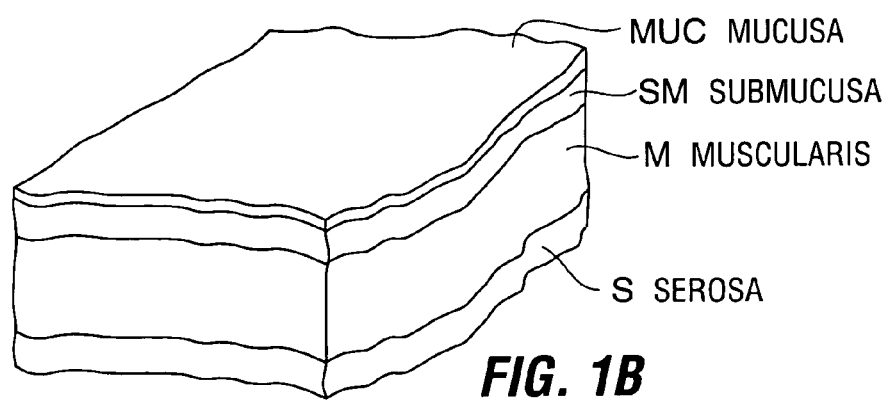
FIG. 1B is a cross-sectional perspective view of a portion of a stomach wall, illustrating the layers of tissue forming the wall.
Figure 2A:
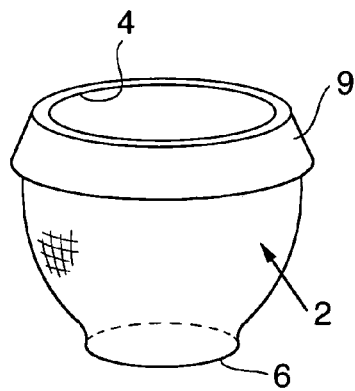
FIG. 2A is a perspective view of a restrictive device of a type that may be used to promote weight loss.

The drawings show a number of methods and components that may be used individually or in combination with one another to facilitate retention of an implant in the stomach or esophagus, including in the gastro-esophageal junction region. These methods and components may facilitate retention by (1) re-shaping tissue or otherwise modifying the structure of the tissue at the implant location in a manner which allows a tissue structure to aid in retaining the implant either with or without a physical connection between the tissue and the implant; (2) anchoring the devices in place; and/or (3) facilitating even distribution of forces (e.g. forces resulting from food pressure or stomach motility) around the implant to minimize the chance of tissue erosion at points where the implant contacts or is anchored to tissue. This application also describes alternative embodiments to the restrictive device 2 of FIG. 2A.

For the purposes of this application, the terms "restrictive devices", "satiation devices," "obstructive devices" or "satiation pouches" will be used to mean devices or pouches intended to induce weight loss in one or more of a variety of ways. These include, but are not limited to, slowing the rate at which food passes from the esophagus into the stomach, physically restricting the amount of food that can be consumed, and/or imparting pressure against portions of the body (e.g. stomach, esophagus, esophageal sphincter, etc) causing the patient to experience sensations of fullness, and/or affecting levels of hormones or other substances in the body that control or affect feelings of hunger, and/or affecting the amount of ingested food absorbed by the body. The anchoring devices and methods described herein are useful for various types of satiation implants, including those not specifically described herein and including those positionable in the esophagus, the gastro-esophageal junction region and other portions of the stomach including the proximal stomach, fundus, antrum, etc.

It should be noted that although the embodiments are described in the context of satiation devices, the components and methods described for facilitating retention and/or promoting even distribution of forces may be equally suitable with other types of implants. These implants include, but are not limited to prosthetic valves for the treatment of gastroesophageal reflux disease, gastric stimulators, pH monitors and drug eluting devices that release drugs, biologics or cells into the stomach or elsewhere in the GI tract. Such drug eluting devices might include those which release leptin (a hormone which creates feelings of satiety), Ghrelin (a hormone which creates feelings of hunger), octreotide (which reduces Ghrelin levels and thus reduces hunger), Insulin, chemotherapeutic agents, natural biologics (e.g. growth factor, cytokines) which aid in post surgery trauma, ulcers, lacerations etc. As yet another example, the implant may provide a platform to which specific cell types can adhere, grow and provide biologically-active gene products to the GI tract. As other alternatives, an implant may provide a platform for radiation sources that can provide a local source of radiation for therapeutic purposes, or provide a platform whereby diagnostic ligands are immobilized and used to sample the GI tract for evidence of specific normal or pathological conditions, or provide an anchor point for imaging the GI tract via cameras and other image collecting devices.

It should also be noted that the embodiments described herein have broad applicability for retaining implants in parts of the body outside the GI system. The term "implant" will thus be used to refer to satiation devices as well as other types of medical devices that may be implanted in the esophagus, gastro-esophageal junction, stomach, elsewhere within the GI tract, or in other hollow organs, vessels, and cavities of the body.

Retention Methods Utilizing Re-Shaping Techniques

FIGS. 3-24 illustrate implants and implantation techniques which minimize or largely avoid connecting the implant and body tissue using connectors (i.e. sutures, staples, clips etc.) that both penetrate the surface of the body tissue and physically connect to the implant. In these embodiments, a portion of the implant is captured by a tissue structure formed within the body by re-shaping body tissue. As will be appreciated from the description that follows, such tissue structures may be strictures created in the stomach to retain the device, or they may be pockets, tunnels, ledges or other barriers against implant migration formed by attaching regions of tissue and/or creating plications in the stomach tissue. The tissue structures may be formed using endoscopic procedures passed through the esophagus into the stomach, and/or using laparoscopic or surgical procedures.

Figure 3:
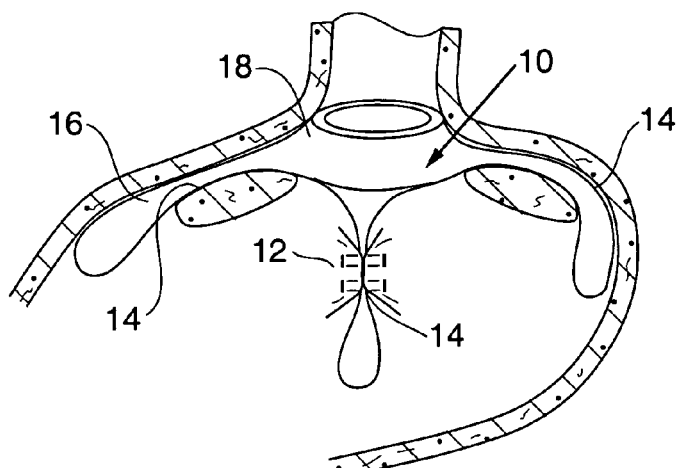
FIG. 3 is a perspective view illustrating a restrictive device retained by tissue structures in the proximal portion of a human stomach.
Figure 4E:
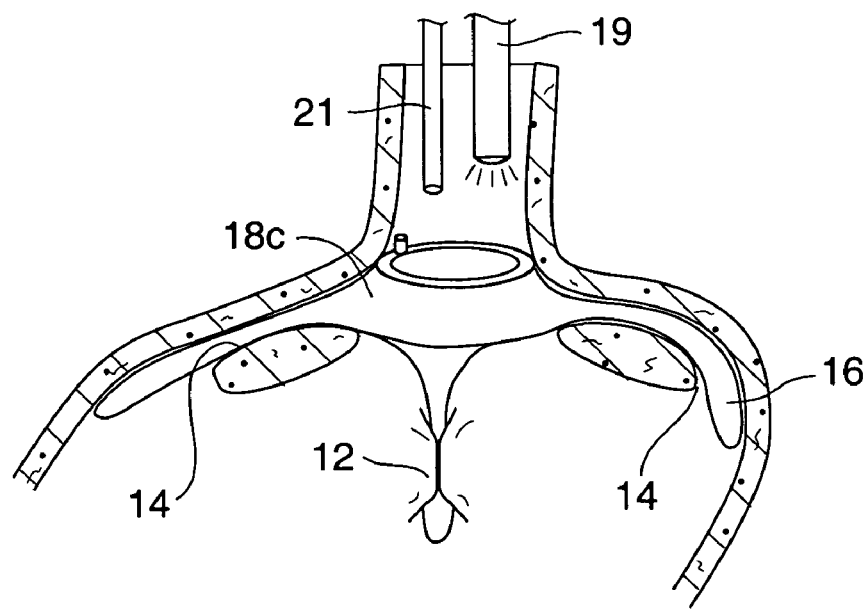
FIG. 4E is a perspective view similar to FIG. 3 showing an inflatable restrictive implant retained within the gastro-esophageal junction region. Also shown are an inflation tube and an endoscope.
Figure 4F:
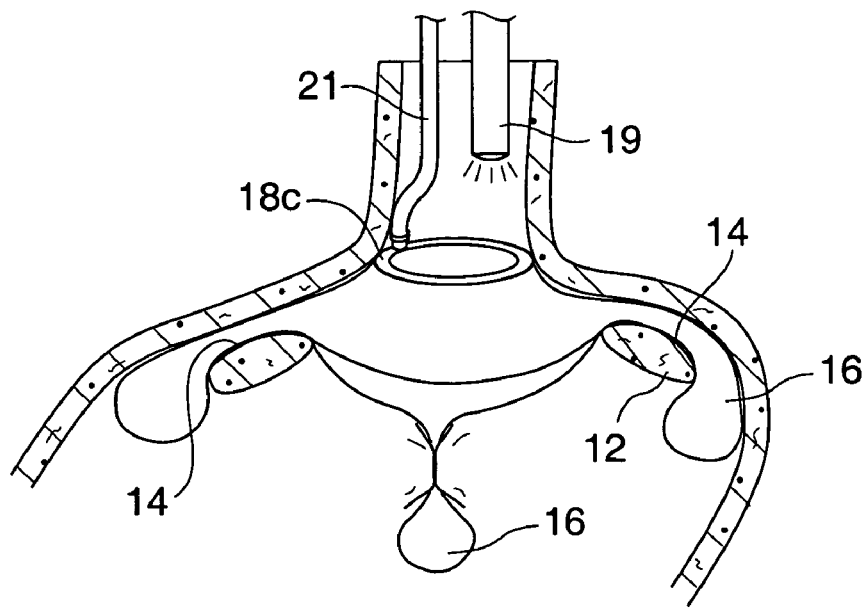
FIG. 4F is similar to FIG. 4E but shows the implant following inflation, with the inflation tube still attached to the restrictive implant.

FIG. 3 shows a restrictive implant 10 being retained by plications 12 formed in stomach tissue. The plications may be formed by grasping sections of tissue and suturing the tissue together to form pocket-like tissue structures 14. Such structures are pocket-like in the sense that they have an interior space bounded by tissue, and at least one opening extending into the interior space. The interior walls of the pocket may lie in contact with one another, collapsing the interior space in the same way the space within a shirt pocket is collapsed. The pockets may also be tunnel-like in the sense that there may be openings on opposite sides of the interior space so that an instrument or portion of a medical device may be passed through the pocket. If necessary, more than two such openings may be provided in the pocket. In other embodiments, the pockets may be more tubular or tunnel-like.

The implant 10 includes leg members 16 that are retained within the pockets 14 of the plications 12. During implantation, the leg members may be inserted into the pockets 14, or the implant may be positioned before the plications are formed, in which case the placations 12 may be formed around the leg members 16.

Restrictive implant 10 includes a restrictive component 18 which may be any configuration that slows the passage of food into the stomach, such as by reducing the effective cross-sectional area of the flow path between the esophagus and stomach or between one region of the stomach and another region of the stomach. For example, the restrictive component may be a pouch similar to see pouch 2 of FIG. 2A, or a restrictive ring 18a (see FIGS. 3, 4A, 4B) or a notched disk 18b (FIGS. 4C and 4D), or a mesh screen. The restrictive component might also be a partially obstructive balloon 18b that may be implanted in a deflated condition under visualization using an endoscope 19 (FIGS. 4E and 4F), and then inflated using an inflation tube 21 coupled to a source of inflation medium such as air or gas. The balloon 18b may be torroidal etc so as to include an opening for passage of food, or it may be shaped to permit flow of food around its exterior. As yet another alternative, a ring such as ring 18a FIGS. 4A and 4B may be provided, and an additional restrictive component (e.g. an obstructive member such as a pouch, disk, balloon, etc.) may be separately attachable to the ring before or after implantation. An examples of this type of configuration is shown in FIG. 37E. This allows the physician to select and alter the amount of restriction needed for a particular patient.

The leg members 16 may be long enough to be retained in tissue pockets formed well into the stomach, such as in the antrum, the fundus or other regions of the stomach while still positioning the restrictive orifice of the device in the proximal stomach. Alternatively, the leg members 16 may be shorter for retention by plications in the gastro-esophageal junction region or other proximal portions of the stomach. This concept of retaining the implant using tissue plications may be applied to implants positionable in other regions of the stomach (and throughout the body) as well, and is not limited to use with implants that provide restriction in the proximal stomach.

Implant 10a of FIG. 4A includes retention elements such as soft stops 24 at the ends of members 16a. These elements deform for passage into a pocket and expand upon exiting the pocket. Inflatable retention elements may likewise be used. As another alternative shown in FIG. 4B, the soft stops may be replaced with barbs or hooks 24a that are deployed through the pockets 14 in a straight orientation and that are deformable or adjustable to a curved orientation following deployment to facilitate retention.

Formation of Pockets

The orientation of the pockets may be selected depending on the purpose to be achieved by the plications and/or the orientation of the implant to be retained. Referring again to FIG. 3, pockets 14 may be formed to have a more vertical orientation (i.e. more or less radiating away from the gastro-esophageal junction) as opposed to the more horizontal pockets shown in later drawings which may line up somewhat circumferentially around a portion of the stomach. Referring to FIG. 5A, the pockets 14 may comprise plications 12 created by drawing folds 20 of tissue around a mandrel 22 within the stomach, and then attaching the folds together using sutures 24. The mandrel may then be removed, leaving a pocket 14 in its place. Afterwards, legs 16 of the implant 10 are inserted into the pocket 14 as shown in FIG. 5B. Over time, the regions of tissue held in apposition will adhere together due to the body's physiological or biological response, such as formation of fibrous tissue or scar tissue, growth of new tissue, or a growing, healing, or knitting together of the opposed tissue layers. The term "adhesion" will be used in this application to refer to the adhering of opposed tissue layers as a result of any physiological or biological response, including but not limited to those listed above.

Figure 6C:
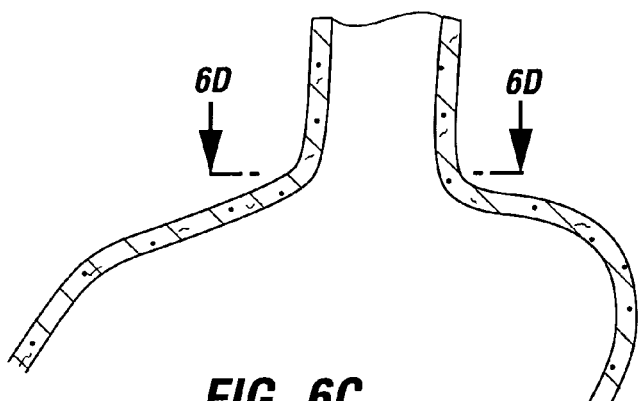
FIG. 6C is a cross-sectional side view of a proximal stomach.

FIG. 6A illustrates formation of plications 12 using a surgical stapler 28 approaching the exterior surface of the stomach in a laparoscopic or open surgical procedure. As shown, the stapler 28 is provided with staples 30 in the distal most portion of its jaws, but there are no staples in the more proximal portion 32 of the jaws. To form a plication, the jaws are clamped onto a section of stomach tissue and staples 30 are passed through the tissue. As shown in FIG. 9B, the section of tissue 34 that was within proximal portion 32 (FIG. 6A) of the jaws is not stapled, and thus forms a tissue pocket 14. Referring to the top cross-section view of FIG. 6D, several such tissue pockets 14 may be formed around the stomach so that portions of a restrictive device (such as leg members 16) may be positioned within the pockets 14 as shown in FIG. 3. As will be discussed in greater detail below, the manner of joining the tissue to form the tissue plications should be chosen to allow the plications to withstand the expansion forces F (FIG. 6D) that occur along the stomach walls.

Figure 7:
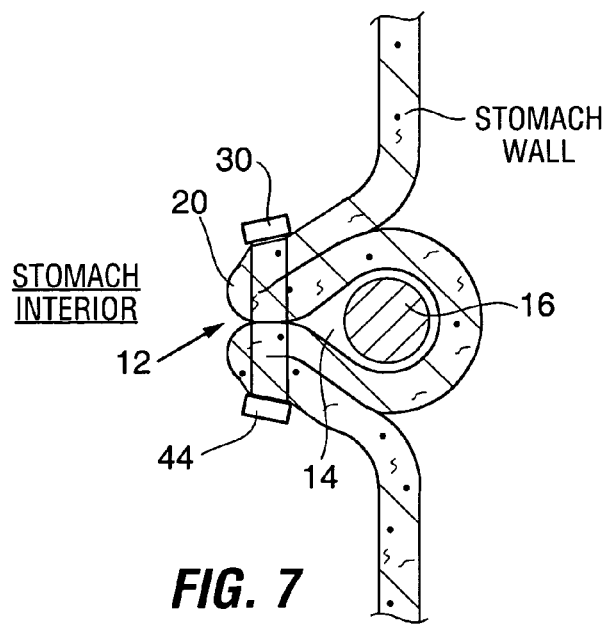
FIG. 7 is a cross-section view of a portion of a stomach wall, showing a modification to the FIG. 6A-6B arrangement in which the tissue pocket is formed from within the stomach.

FIG. 7 is a top cross-section view of a portion of a stomach wall, illustrating that the vertical plications 12 may be formed from within the stomach (e.g. endoscopically using access through the esophagus) to create tissue pocket 14. This may be performed using an endoscopic staple, suturing device, or clip applier introduced transorally into the stomach.

Figure 8A:
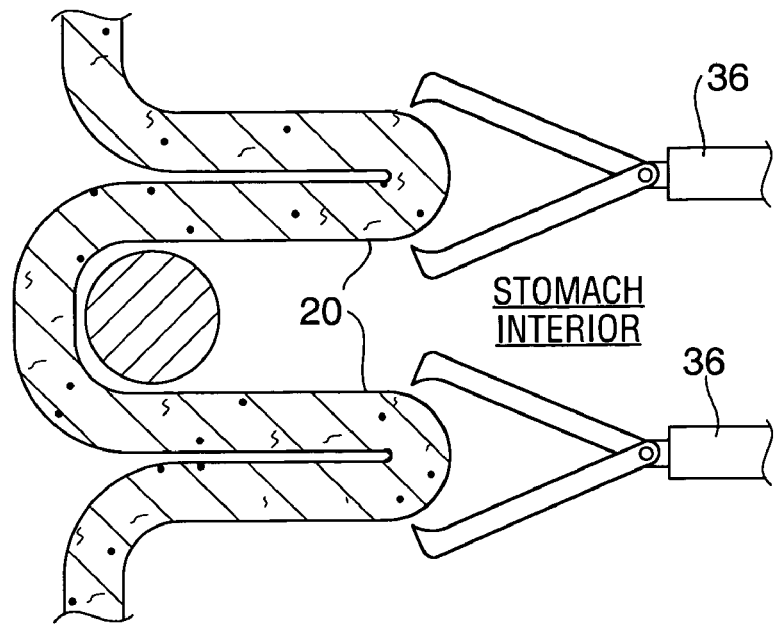
FIGS. 8A and 8B are a cross-sectional side view of a stomach wall illustrating methods for drawing tissue together to form plications in the stomach wall.
Figure 8B:
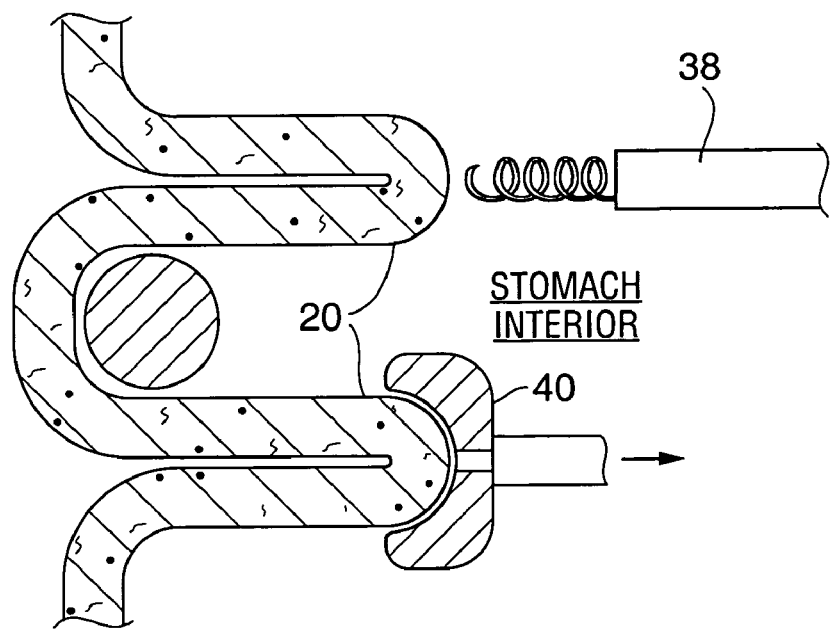

FIGS. 8A and 8B illustrate methods of forming a tissue pocket such as that shown in FIG. 7 using endoscopic devices passed into the stomach via the esophagus. These methods may also be performed using a surgical or laparoscopic approach through the stomach wall.

According to these methods, an endoscopic grasper 36 (FIG. 8A), corkscrew mechanism 38 (FIG. 8B), vacuum device 40 (FIG. 8B) or alternative device is passed through the stomach via the esophagus and used to pinch folds 42 of tissue, on the interior stomach wall. Sutures (or clips, staples etc.) are passed through the folds 42 to draw the folds into contact with one another into the configuration shown in FIG. 7. It may be desirable to add rows 46 of sutures or staples through each fold 42 before the folds are joined together, as shown in FIG. 8C.

The sutures/staples etc. may optionally be passed through patches or strips 44 (FIG. 7) of buttressing material such as bovine pericardium strips, Teflon strips or polycarbonate strips so as to facilitate retention of the staples/suture within the body tissue until such time as the contacting tissue layers adhere together. Alternatively, pledgets, t-bars, etc. of the type described in connection with FIGS. 26A-30B may be used to buttress the sutures/staples until such time as tissue adhesion occurs.

Over time, adhesions form between the tissue surfaces held in contact by the sutures, thereby creating a much stronger bond between the tissue surfaces than would be achieved using sutures alone. If desired, dissolvable or bioabsorbable sutures may be used to create the plications.

Figure 8C:
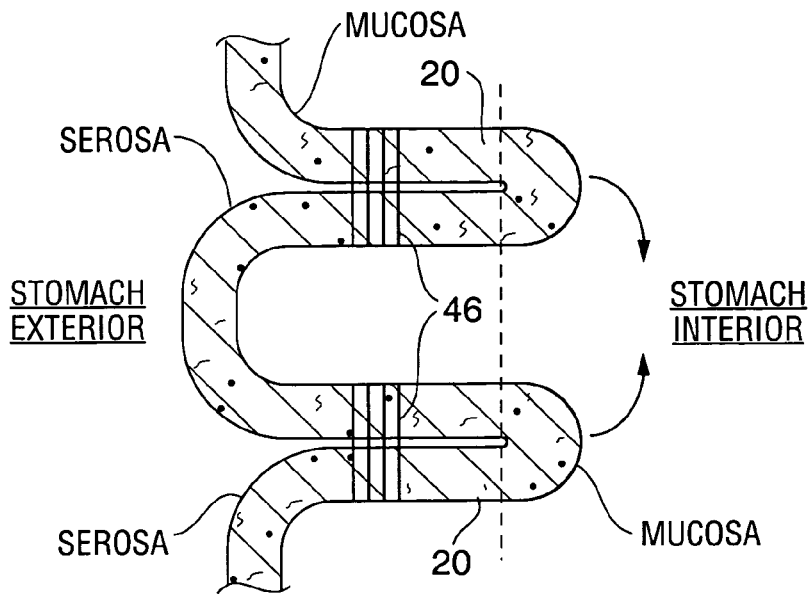
FIGS. 8C and 8D are similar to FIGS. 8A and 8B further illustrate methods of attaching the folds of tissue that have been drawn together to form a tissue pocket.

The procedure illustrated in FIGS. 8A through 8C is particularly advantageous in that it relies in part on adhesion of the serosal tissue lining the outer surface of the stomach. It has been found that serosal tissue layers can adhere to form relatively strong bonds when held in apposition to one another. Because the procedure of FIGS. 8A-8C also strives for adhesion of some interior stomach tissue after tissue folds or tabs 20 are attached together, modification of the interior tissue surface may further be needed in order to optimize adhesion of opposed regions of internal stomach tissue. In particular, it is believed that better adhesion of the interior wall surfaces may be achieved when a portion of the mucosal layer of tissue lining the stomach interior is removed, such that the tissue surfaces sutured in apposition to one another are serosal, sub-mucosal or muscularis layers. It is believed that opposed layers of mucosal tissue do not adhere together as well as opposed layers of serosal, sub-mucosal, or muscularis tissue.

Figure 8D:
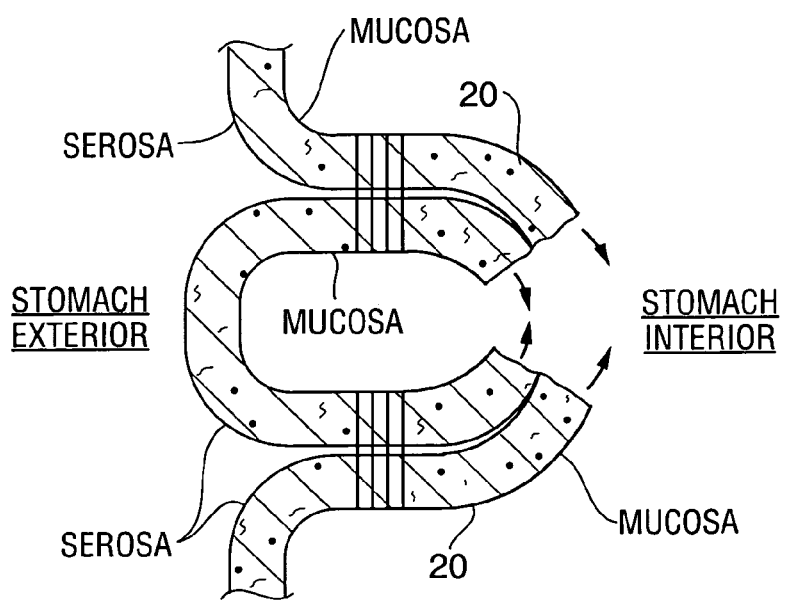

Referring to FIG. 8C, one surface modification method for promoting tissue adhesion includes cutting, ablating (using RF, laser, or chemical ablation) or abrading the mucosal surface of each tissue fold 20 within the stomach as indicated by dashed lines. This modification is ideally performed before the folds are placed in apposition and sutured together. Depending on the depth to which cutting, ablation or abrasion is performed, the sub-mucosal, musclaris, or serosal layer beneath the mucosal layer is exposed, and the corresponding abraded/cut sections of each fold are placed in apposition and sutured/stapled together as indicated in FIG. 8D. This allows the exposed regions of tissue to be sutured together and causes the opposed surfaces to tightly adhere over time. During the procedure, it may be helpful for the physician to mark the exposed tissue regions using dyes or other markers to allow the tissue to be easily identified when it is time to position the exposed regions in apposition to one another.

Figure 8E:
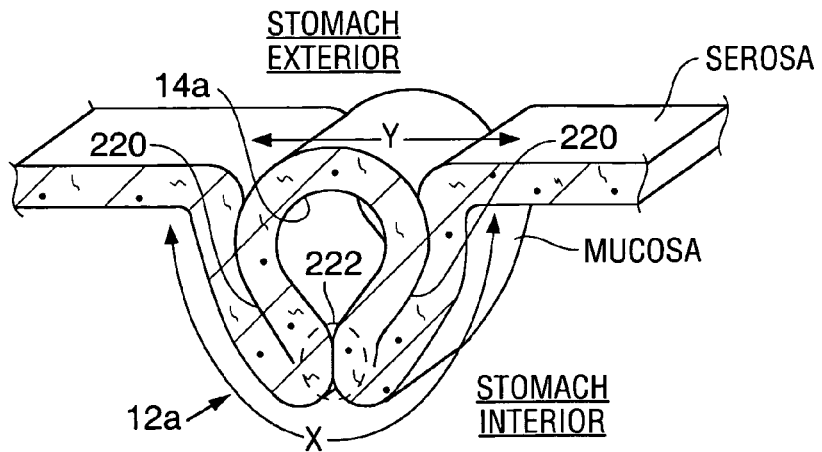
FIGS. 8E through 8G are cross-sectional top views of a portion of a stomach wall, illustrating various configurations of plications that may be formed to create tissue pockets.
Figure 8F:
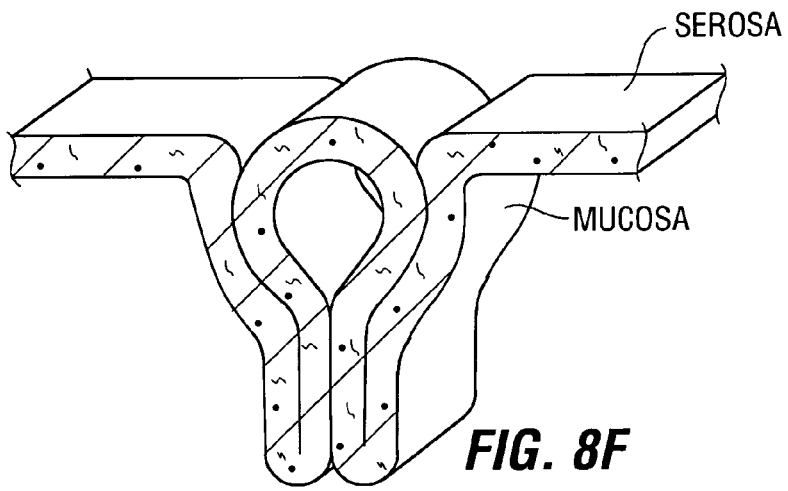
Figure 8G:
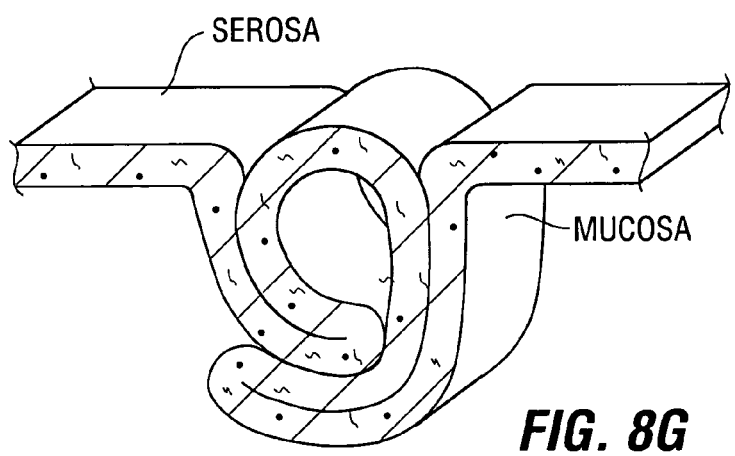

FIG. 8E is a perspective view of a plication 12a and tissue pocket 14a formed using the method described in connection with FIGS. 8A through 8D. As can be seen, the plication includes long serosal contact lines 220. The mucosal or sub-mucosal contact line 222 (assuming tissue modification as shown in FIG. 8D) is relatively small. Because an adhesion which forms along the serosal contact line 220 is believed to be stronger than adhesions which form along the mucosal or submucosal contact line 222, it is desirable to proportion the plication such that the dimension identified by arrow "X" is greater than the dimension identified by arrow "Y". This configuration allows the greatest of the forces imparted against the stomach (see forces F of FIG. 6D) to be borne by the serosal adhesion. As illustrated in FIG. 8F, an elongated versions of the plications of FIG. 8E may be formed to further extend the length of the contacting regions so as to optimize the strength of the adhered tissue. Another configuration resulting from even longer adhesions is illustrated in FIG. 8G.

Figure 9A:
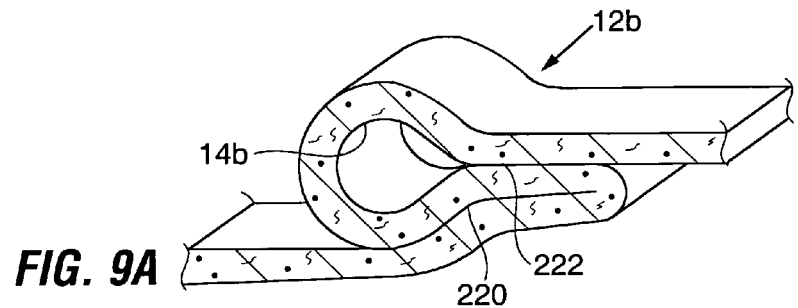
FIG. 9B is a cross-section view of a stomach similar to FIG. 6D, illustrating an alternate form of plication used to create tissue pockets. A more detailed view of one of the pockets of FIG. 9B is shown in FIG. 9A.
FIG. 9C is a cross-sectional top view of a portion of a stomach wall showing yet another plication arrangement for forming a tissue pocket.
Figure 9B:
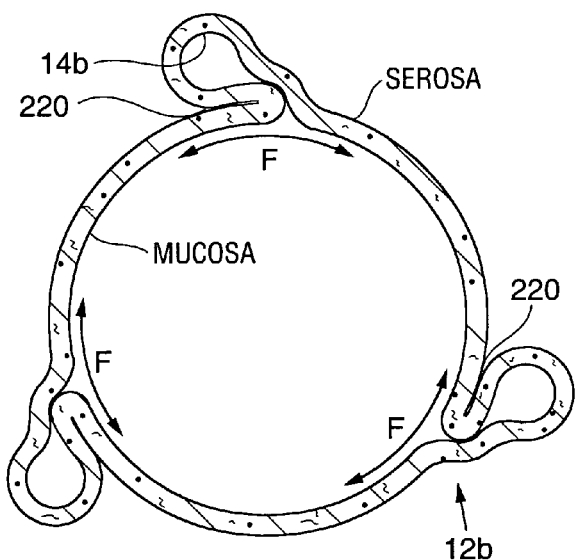

FIG. 9A illustrates another configuration of a tissue pocket 14b which relies in large part on regions of serosal contact 220 and relatively smaller regions of mucosal or submucosal contact 222. In addition, as illustrated in FIG. 9B, the contact lines which result in adhesions are oriented "in shear" relative to the primary forces F experienced by the stomach, and thus may be less likely to pull apart in response to such forces. This is in contrast to the pockets 14 FIG. 6D in which the contact lines are oriented "in peel" relative to the forces F.

Figure 9C:
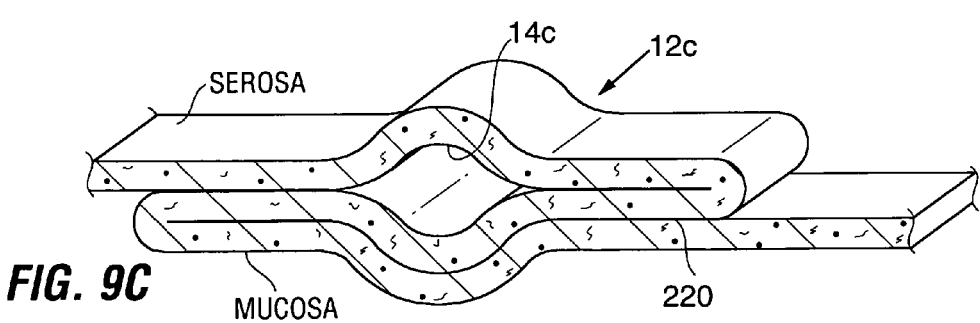

FIG. 9C illustrates another configuration of tissue pocket 14c in which the contact lines forming plications 12c are oriented in shear. This configuration utilizes three plication folds and forms a very long region of serosal contact 220.

Figure 6D:
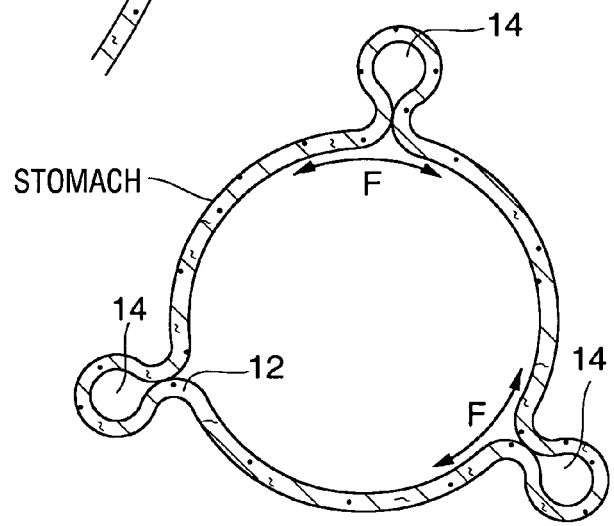
FIG. 6D is cross-section view taken along the plane designated 6D-6D in FIG. 6C, illustrating one form of plication formed in the stomach wall to create tissue pockets.
Figure 10A:
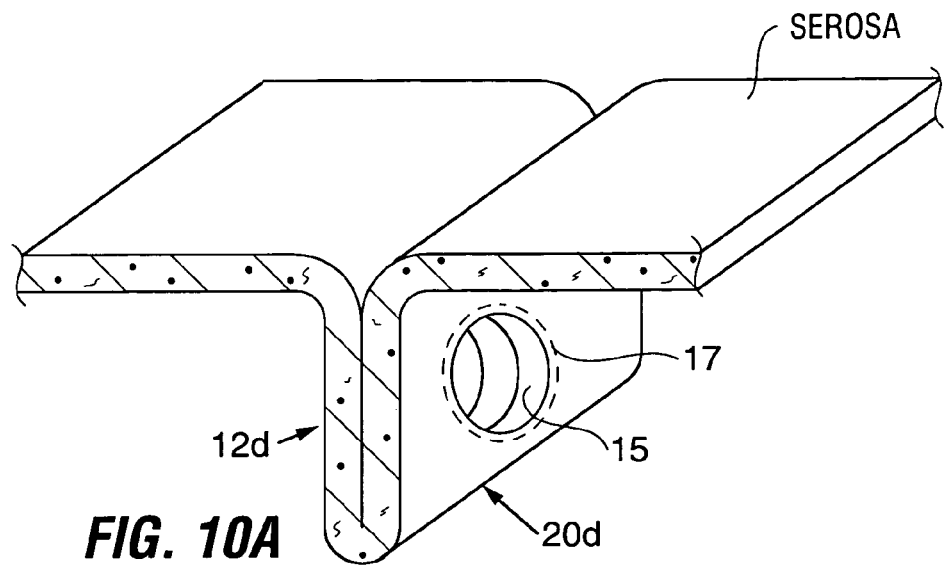
FIG. 10A is a cross-sectional perspective view of a portion of stomach wall, showing yet another type of plication that may be used.
Figure 36A:
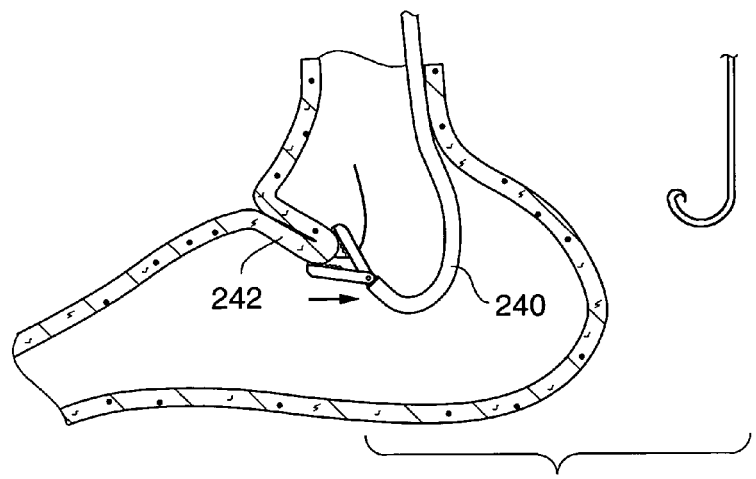
FIGS. 36A through 36E are a sequence of cross-section views of a stomach illustrating a method of re-shaping tissue to form a circumferential plication, and using the circumferential plication to retain an implant.

FIGS. 10A, 11D, and 36A illustrate alternative forms of tissue structures that may be formed, in which the serosal contact lines form an adhesion that is in peel, but that differ from the FIG. 6D plications in that they utilizes a serosal adhesion line rather than a mucosal adhesion line.

Figure 10B:
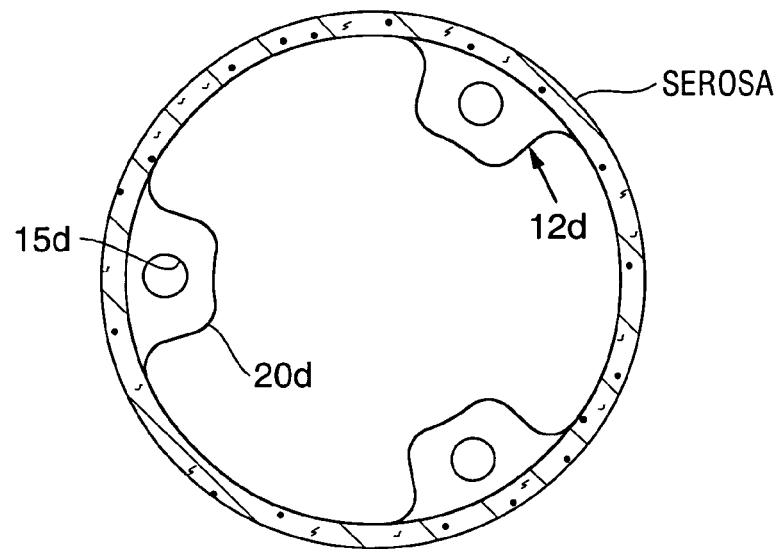
FIG. 10B is a cross-sectional top view of a stomach, similar to FIG. 6D, showing three such plications in the wall of a stomach.

Referring to FIG. 10A, to form plication 12d, tissue within the stomach interior is pinched together to draw serosal layers on the stomach exterior into contact with one another, thereby forming folded tissue tab 20d. A hole 15 is formed in the tab 20d, and staples 17 or sutures, etc., are placed around the hole 15 to keep the tissue pinched together until a serosal adhesion forms. Multiple tabs 20d may be formed as shown in FIG. 10B, and a portion of the restrictive device (such as legs 16 shown in FIG. 3) may be passed into the holes 15 in the tabs to secure the implant within the stomach. Alternatively, an implant may be hung from the tabs 20d using sutures or clips.

As yet another alternative, the FIG. 10A plications may be used without tissue pockets by eliminating the holes 20d and by using sutures or clips to penetrate the tissue and to connect the tissue to the implant. A variation of this alternative is described in connection with FIGS. 3A-36F described below.

To form a structure of the type shown in FIG. 11D, tissue within the stomach interior again is pinched to draw the serosal layers into contact as shown in FIG. 11A, thereby forming a folded tab 20e. Next, staples 17 or sutures etc. are used to define a C-shaped (or similarly shaped) line through the tab 20e. Cuts 21 are formed through the full thickness of the stomach tissue as shown in FIG. 11B. It should be noted that because the cuts 21 are full thickness cuts, the staples 17 are used to seal the stomach interior from the stomach exterior.

After the cuts 21 are formed, the areas of tissue surrounding the cuts 21 are folded downwardly as indicated by arrows in FIG. 11B. The remainder of the tab 20e is opened as shown in FIG. 11D to create a serosal pocket 14e which is accessible from the mucosal (interior) side of the stomach. The serosal tissue forming the interior of the pocket may be lined with a small stent-like device or another liner to protect it from stomach acids. Over time, a mucosal tissue layer may grow over this serosal interior of the pocket (and/or over the stent or liner) and thereby further protecting it from the acidic stomach environment.

Figure 12A:
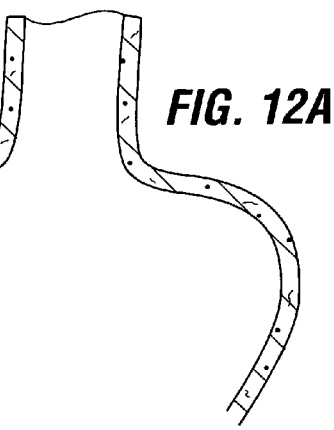
FIGS. 12A through G are a sequence of cross-sectional perspective views of a proximal portion of a stomach, illustrating another method for forming plications to create tissue pockets.
Figure 12B:
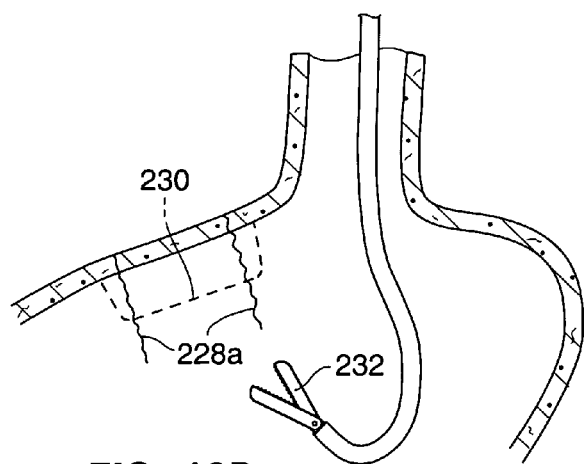

FIGS. 12A through 12G illustrate another method of forming tissue pockets that take advantage of the strong adhesions formed when serosal tissue surfaces are held in apposition. Referring to FIG. 12A, a rod 226 is positioned on the exterior surface of the stomach, and sutures 228 are attached to the rod 226 and passed through the stomach walls. The sutures 228 are drawn inwardly using an endoscopic grasper (not shown) to "tent" a section 230 of tissue of the type shown in FIG. 12C. If desired, the rod 226 may be eliminated, in which case a pair of sutures 228a may be passed from the stomach interior, through the stomach wall, and then back into the stomach interior, and then drawn inwardly using an endoscopic grasper 232 to tent the tissue as shown in dashed lines.

Figure 12C:
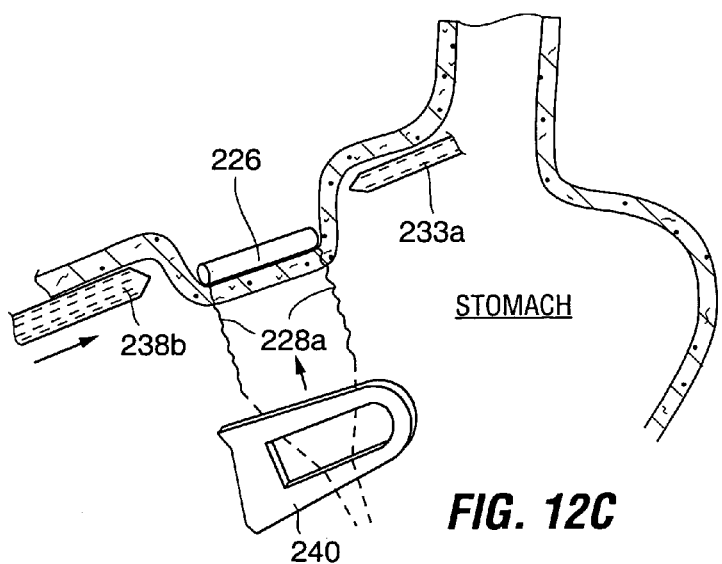
Figure 12D:
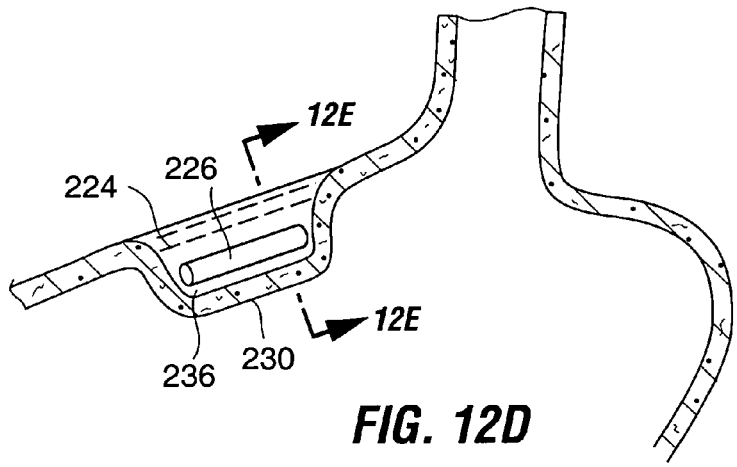

Next, a line 234 of staples or sutures are applied across the tented tissue from the mucosal side of the stomach—thereby forming an enclosed pocket 236 on the exterior surface of the stomach as shown in FIG. 12D. The rod 226 (if used) is enclosed within the pocket 236. Stapling/suturing may be performed using an endoscopic stapler 238a passed through the esophagus into the stomach, or using a laparoscopic stapler 238b introduced into the stomach through a surgical gastronomy site—both of which are shown in FIG. 12C. The stapler/suture device preferably has characteristics that will form a suture/staple line 234 that is sufficiently patent to seal the serosal tissue together to prevent stomach leakage prior to complete serosal adhesion, but that ensures good blood flow so as to promote healing of the stapled tissue. For example, a conventional stapler modified to have a staple cartridge in which alternate staples have been removed may achieve this purpose.

A collar 220 may be placed around the tented tissue 230 as shown in FIG. 12C prior to suturing/stapling so as to apply tension to the wall tissue to facilitate suturing or stapling.

Figure 12E:
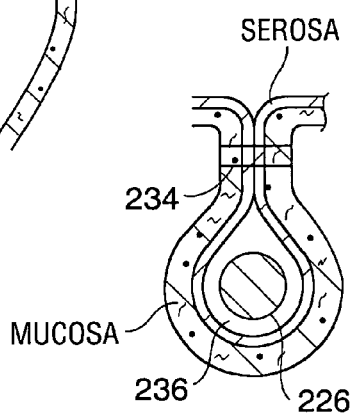
Figure 12F:
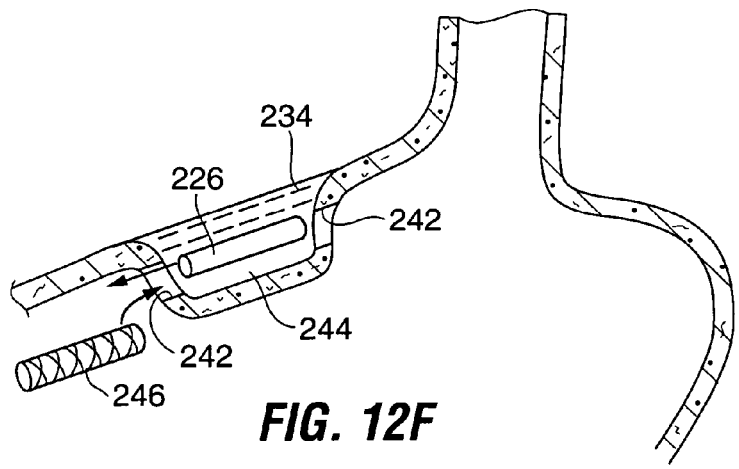
Figure 12G:
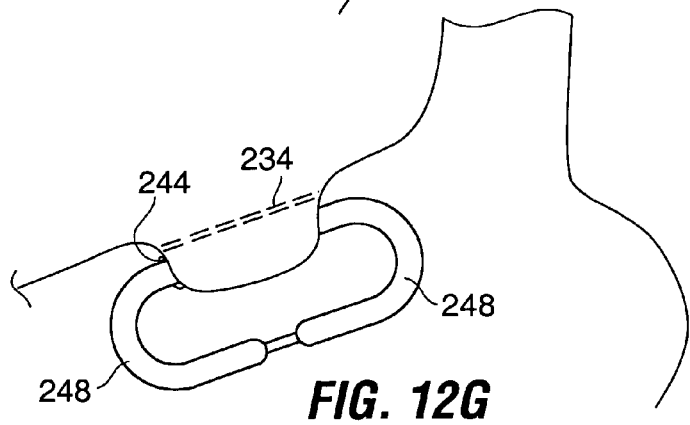

The suture line 234 holds the serosal layers of tissue together as shown in FIG. 12E, thereby holding the pocket 236 together. The ends 242 of the pocket are cut, turning the pocket 216 into a tissue pocket 244 having ends that open into the stomach interior. The rod 226, if used, is removed from the pocket 244. As with the other embodiments, the tissue preferably heals together to form an adhesion that maintains the pocket.

Because the tissue pocket 244 is formed of serosal tissue, it may be desirable to line the pocket 244 with a stent-like device 246 or another liner to both reinforce the pocket and protect the serosal surface from the acidic stomach environment.

As with the other embodiments, the procedure continues with formation of as many pockets as are needed to retain the desired implant in the stomach. Then, implants (or portions of implants) are fed into the pockets for retention within the stomach. As one example, legs 16 of a device such as device 10 (FIG. 3) may be extended through the pockets. Alternatively, other forms of implants (e.g. capsules containing diagnostic or therapeutic agents or devices, c-bars 248 of FIG. 12G to which implants or space occupying devices may be attached) may be positioned within the pockets 244. A drug-eluting capsule or similar implant may be proportioned to fit in its entirety within the pocket form using this or other methods. The openings in the pocket may be closed following insertion of the capsule such that drugs eluted by the capsule pass through the walls of the pocket and into the stomach.

As a third alternative, a member may be positioned in a pocket and tethered to a gastric balloon or other space-occupying device used in for inducing weight loss, or to another type of medical device such as a therapeutic or diagnostic device.

Tissue Surface Modification

As discussed in connection with FIGS. 8C and 8D, when interior stomach surfaces are to be placed in apposition so as to induce adhesion, it may be advantageous to modify the tissue surface so that submucosal, serosal, or muscularis tissue (rather than mucosal tissue) is used to form the adhesion. FIGS. 13A through 14B illustrate various methods for altering the interior stomach surface for this purpose.

As one example, a single device may be used to modify regions of surface tissue and to join modified tissue surfaces. FIGS. 13A and 13B, illustrate a cutting and suturing device 48 that may be used for slicing a layer of tissue from the interior of the stomach and passing a suture through a portion of the remaining tissue. In particular, the device can modify neighboring surface regions of tissue, and then drawing the modified surface regions into contact with one another to promote adhesion and to form a tissue pocket.

Referring to FIG. 13A, device 48 includes an elongate shaft 50 extending from a handle 52. Means is provided in the handle 52 for articulating the shaft 50 in one or more planes using methods known to those skilled in the art.

Referring to FIG. 13B, a recess 54 is formed in the distal end of the device 48. A suture lumen 56, a needle lumen 58, and a cutting blade lumen 60 extend through the shaft 50 and separately open into the recess. The device may optionally be provided with a vacuum source (not shown) that allows a vacuum to be applied to draw tissue into the recess 54. For this purpose, a fourth lumen having a plurality of inlets exposed to the interior of the recess may be provided and be connectable to a vacuum source.

A suture 62 is disposed within the suture lumen 56. The suture 62 has a suture catch 64 on its distal end, positioned adjacent to the opening of the lumen 56 into the recess 54. A suture needle 66 is slidable within the needle lumen 58. The needle lumen 58 and suture lumen 56 are oriented such that during operation needle 66 may be extended from the needle lumen 58, through tissue disposed within the recess and into engagement with the suture catch 64. As will be described in further detail below, subsequent retraction of the suture needle 66 carries the suture catch 64 and the end of suture 62 through the tissue and into needle lumen 58.

A cutting blade 68 is slidable within the cutting blade lumen 60 to shave a layer from tissue disposed within the recess 54. The handle 52 (FIG. 13A) includes actuators (not shown) for extending and retracting both the cutting blade 68 and the needle 66.

Use of the device 48 will next be described with reference to FIGS. 13C through 13H.

First, the device 48 is introduced into the stomach under endoscopic visualization. The device 48 is placed into contact with the target stomach tissue, and tissue is drawn into the recess 54. This may be accomplished by pressing the recess 54 against the tissue surface, or by activating a vacuum source configured to draw tissue into the recess 54. As discussed previously and as indicated in FIG. 13C, the tissue is comprised of several tissue layers: the mucosa MUC which lines the stomach interior, the submucosa SM beneath the mucosa MUC, the muscularis M, and the serosa S which lines the stomach exterior. The dimensions of the recess 54 and the position of the blade 68 are chosen such that tissue will be drawn into recess 54 by an amount that will appropriately align the tissue layer(s) to be removed with the blade 68. In preferred examples, the mucosa MUC will be removed to expose the submucosa SM or both the mucosa and submucosa SM will be removed to expose the muscularis M. For purposes of illustration, removal of the mucosa MUC will be described in connection with FIGS. 13C through 13F.

Figure 13C:
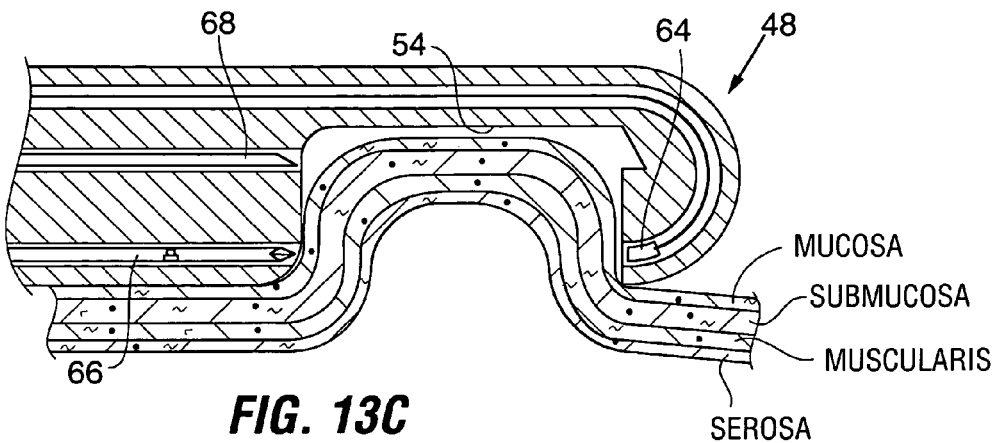
Figure 13D:
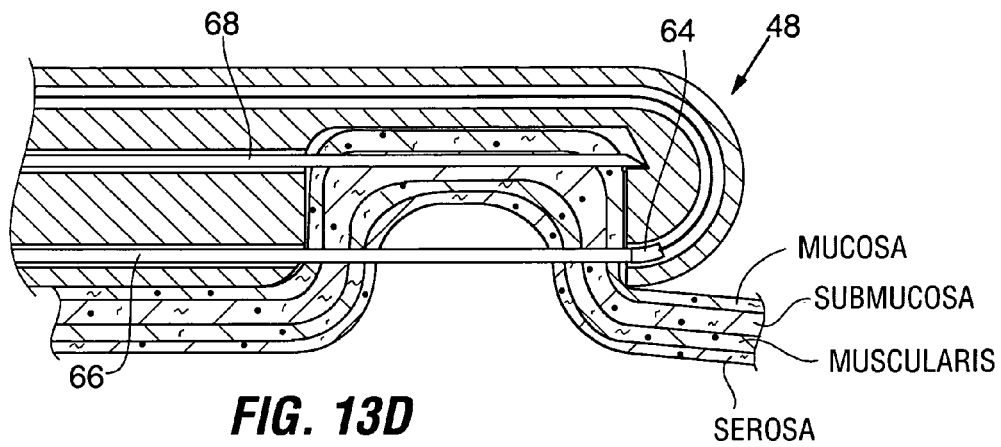
Figure 13E:
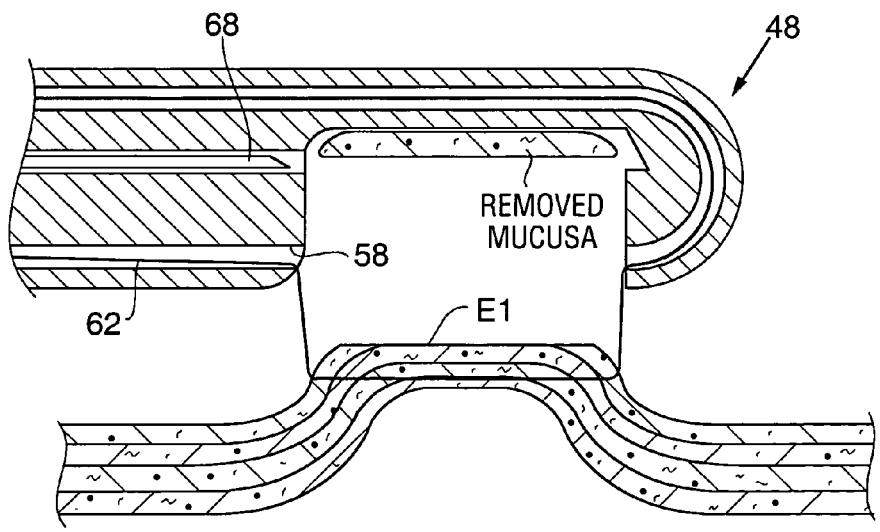

Once tissue has been drawn into recess 54, the cutting blade 68 is advanced (FIG. 13D) into the recess 54 to shave off the mucosa MUC, thereby leaving an exposed region E1 of submucosa (FIG. 13E). A source of RF energy (not shown) may be electrically connected to the cutting blade 68 to coagulate tissue during or after resection, so as to reduce bleeding and promote tissue healing. If ablation energy is used, a grounding electrode is positioned in contact with the patient during use of the device.

Next (or simultaneously with advancement of the cutting blade 68), the suture needle 66 is driven through the tissue, engages with the suture catch 64 (FIG. 13D), and carries the catch 64 and the suture end back through the tissue into the device 48. The tissue is released from the recess 54, and the suture end is retrieved from the proximal end of the device, leaving a loop of suture in tissue as shown.

Next, the process is repeated at an adjacent location (preferably using the same unit of device 48 but alternatively using a second unit), thus creating a second exposed patch E2 of submucosa and placing a second suture 70 through the tissue as shown in FIG. 13F. The exposed patches E1 and E2 of submucosal tissue are brought into contact with one another, such as by pulling the sutures 62, 70, thereby forming tissue pocket 72 (FIG. 13G). The sutures are anchored together to retain contact between the exposed patches. Eventually, the exposed submucosa (or muscularis) surfaces adhere together, forming a strong tissue adhesion that retains the tissue pocket within the stomach. As shown in FIG. 13G, both the interior of the stomach and the interior of the pocket 72 remain lined with healthy mucosa MUC.

Figure 13H:
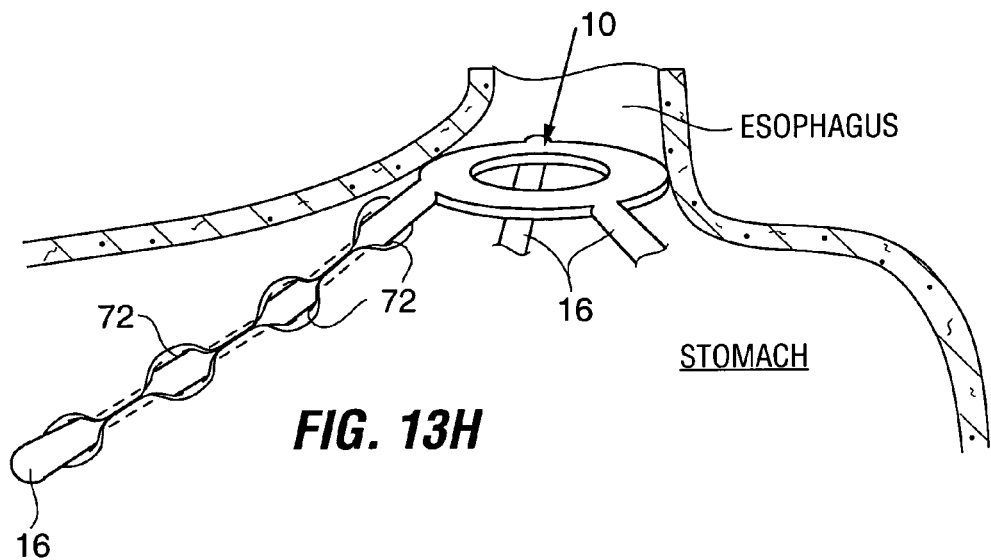
FIG. 13H illustrates positioning portions of a restrictive implant within the tissue pockets.

Referring to FIG. 13H, the leg members 16 of the implant 10 are secured within the tissue pocket 72. This may be done at a later date so as to allow tissue adhesion to occur before the tissue is subjected to loading by the implant. The tissue pockets 72 may be marked using dyes or other markers to allow them to be easily identified when it is time to secure the implant 10.

Depending on the length of the leg members 16, only one or two such pockets 72 may be needed for retaining a leg member 16, or each leg member may be retained by an elongate array of pockets 72 as shown.

Figure 14A:
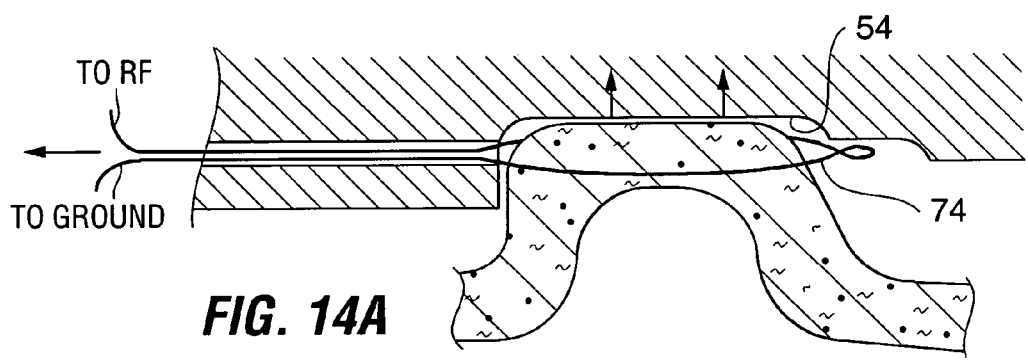
FIG. 14A is a cross-sectional side view of a distal portion of an alternative embodiment of a tissue modification device which uses an ablative wire loop.

Other techniques may also be used for modifying the tissue surface to achieve optimal tissue adhesion between opposed tissue surfaces. Referring to FIG. 14A, the cutting blade 68 of the FIG. 13B embodiment may be replaced with an RF loop snare 74. During use, the loop snare 74 is oriented such that tissue passes into the loop when tissue is drawn into the recess 54. Once tissue is within the recess, the snare (which is energized with RF energy) in retracted in a proximal direction to shave off the target tissue layer.

Figure 14B:
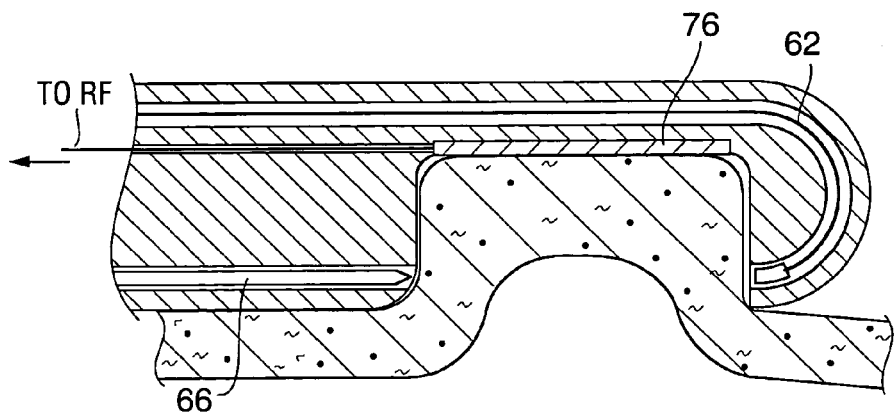
FIG. 14B is a cross-sectional side view of a distal portion of yet another alternative embodiment of a tissue modification device which uses an ablative contact plate.

In another alternative shown in FIG. 14B, the cutting blade is replaced by an RF electrode plate 76 disposed within the recess. Tissue drawn into the recess 54 is thus drawn into contact with the plate 76 and is ablated.

Positioning Implants within Tissue Pockets

Figure 15A:
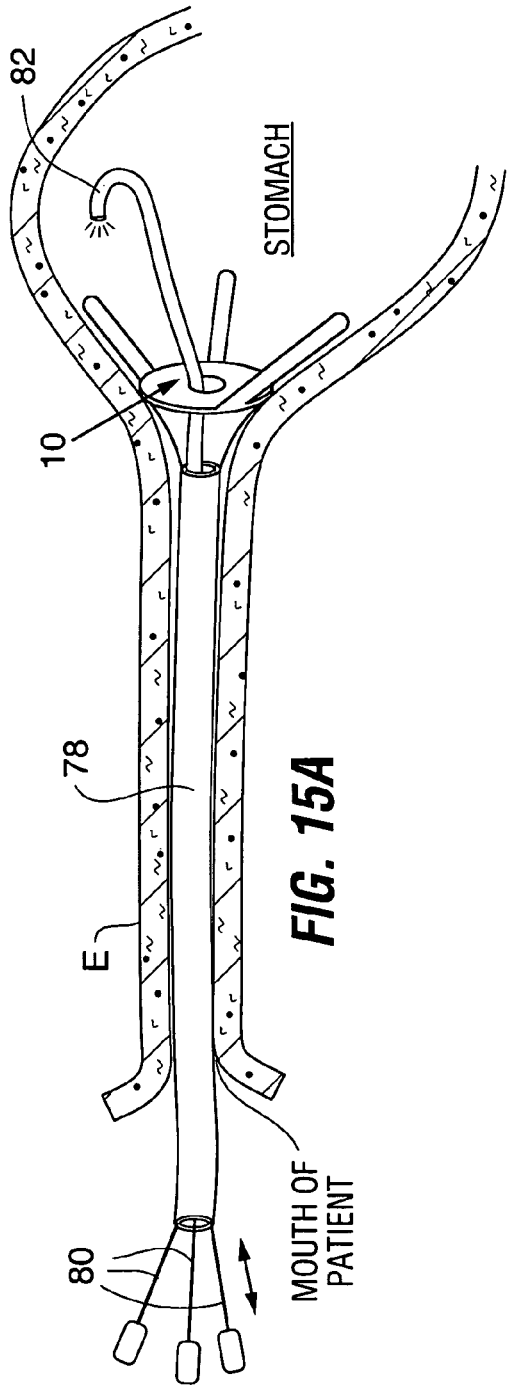
FIGS. 15A and 15B schematically illustrate implantation of a restrictive device of the type shown in FIG. 3.
Figure 15B:
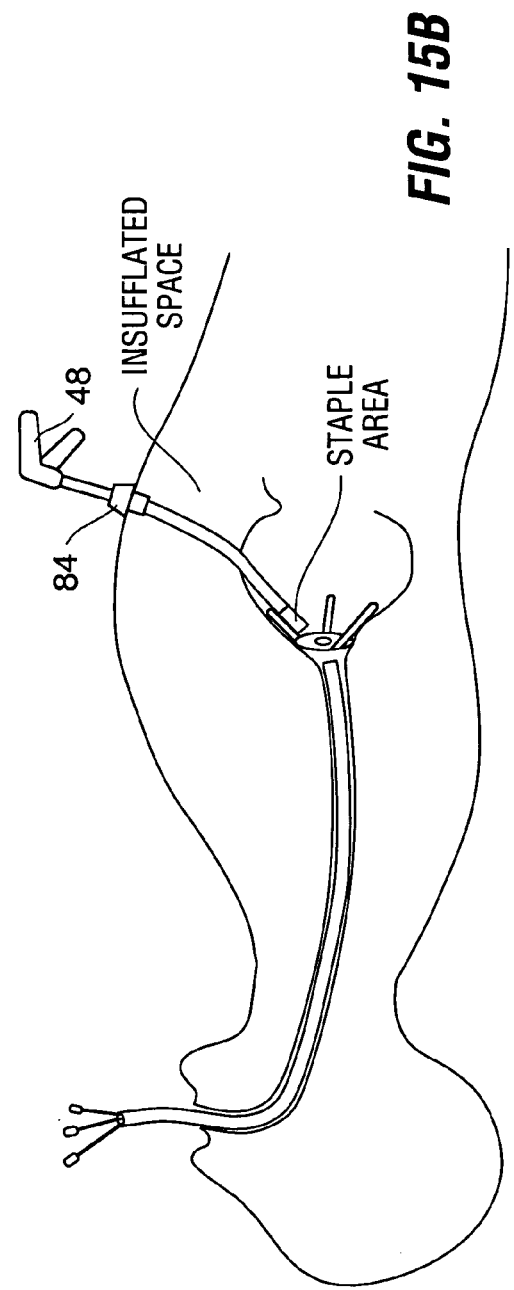

FIGS. 15A and 15B illustrate one method for securing implant 10 using pockets of the type formed with device 48. Referring to FIG. 15A, a hollow guide sheath 78 is passed into the patient's esophagus via the mouth. Implant 10 is passed in a streamlined position through the guide sheath and into the stomach using a plurality of mandrels 80 individually attached to each of the legs 16 and to the implant body 18, if necessary. The mandrels 80 are preferably steerable to allow for manipulation of the legs to the desired positions within the stomach. After the implant 10 enters the stomach, it is allowed or caused to open to its expanded position. An endoscope 82 is passed through the guide sheath 78 and into the stomach.

Laparoscopic incisions are next formed into the abdominal cavity, a trocar 84 is positioned in the incision, and the abdominal cavity is insufflated using procedures well known to those of skill in the art. Suture device 48 (or another type of device such as a laparoscopic stapler or clip applier) is passed through the trocar 84 and used under endoscopic visualization to plicate tissue pockets around the device leg members 16. The laparoscopic procedure is repeated for each of the leg members 16. Naturally, an open surgical procedure may be carried out in place of the laparoscopic procedure. In a less invasive procedure, the suture device 48 may be introduced through the esophagus into the stomach rather than through surgical or laparoscopic incisions.

As discussed previously, it may be desirable to form the tissue pockets 72 before introducing the implant. The preformed tissue pockets 72 may be plicated as described in connection with FIGS. 13D through 13G or using alternative methods.

Figure 16A:
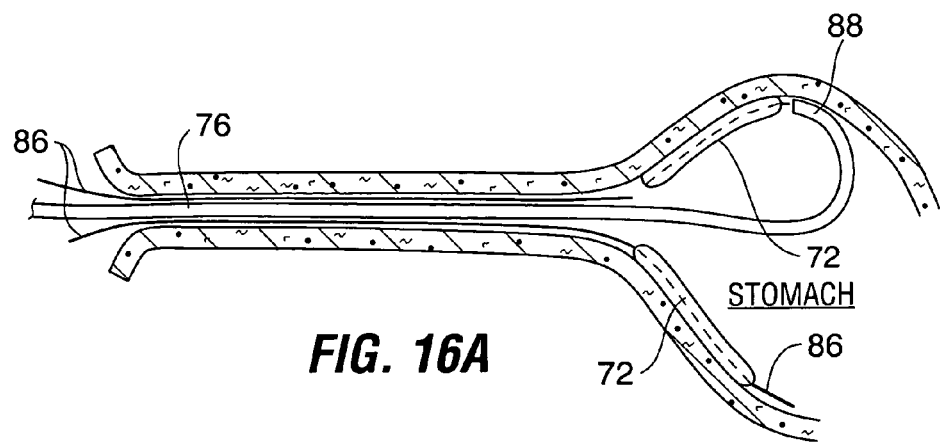
FIGS. 16A and 16B schematically illustrate an endoscopic method for threading portions of a restrictive device into tissue pockets within the stomach.
Figure 16B:
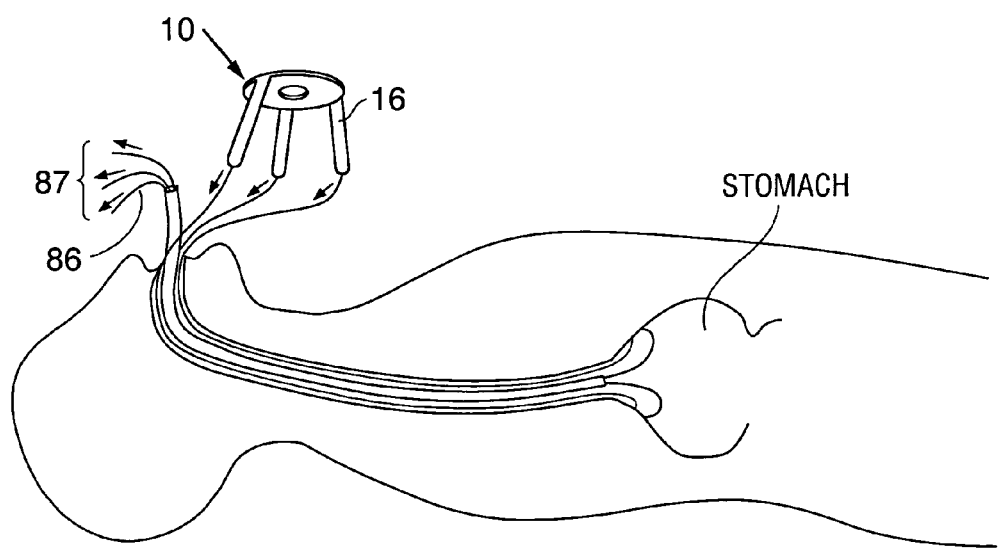

One method of delivering the legs 16 into the tissue pockets 72 is shown in FIGS. 16A and 16B. In preparation for introducing implant 10, the distal ends of a plurality of guidewires 86 are passed down the esophagus into the stomach. The number of guidewires is selected to match the number of legs 16 on the implant 10.

An articulating endoscopic grasper 88 is passed through the esophagus and into the stomach, and its distal end is fed into the distal end of a tissue pocket 72 until it exits the pocket's proximal end. The grasper 88 engages one of the guidewires 86 and pulls the guidewire through the tissue pocket such that the distal end of the guidewire extends out the pocket's distal end. The procedure is repeated for each guidewire. Outside the body, each leg 16 of the implant 10 is attached to the proximal end of one of the guidewires. The grasper 88 then engages the distal ends of the guidewires 86 and draws the distal ends 102 of the guidewires 86 out of the body, thereby towing the implant through the esophagus towards the stomach. As the implant 10 approaches the stomach, the distal ends of the guidewires 86 are individually manipulated to separately draw each leg 16 into a corresponding one of the tissue pockets 72.

Although anchoring of an implant using tissue pockets has been described with respect to implant 10, it should be kept in mind that other types of implants may also be retained using one or more tissue pockets. For example, a drug-eluting capsule may be positioned within a tissue pocket, or a drug-eluting device may include a capsule attached to one or more anchoring members that are retained within tissue pockets. Similar arrangements may be configured for other forms of diagnostic or therapeutic implants of the types mentioned above.

Alternative Methods

FIGS. 17 through 24 and 34A through 36F show alternative ways in which a stomach wall may be re-shaped to facilitate implant retention.

Figure 17:
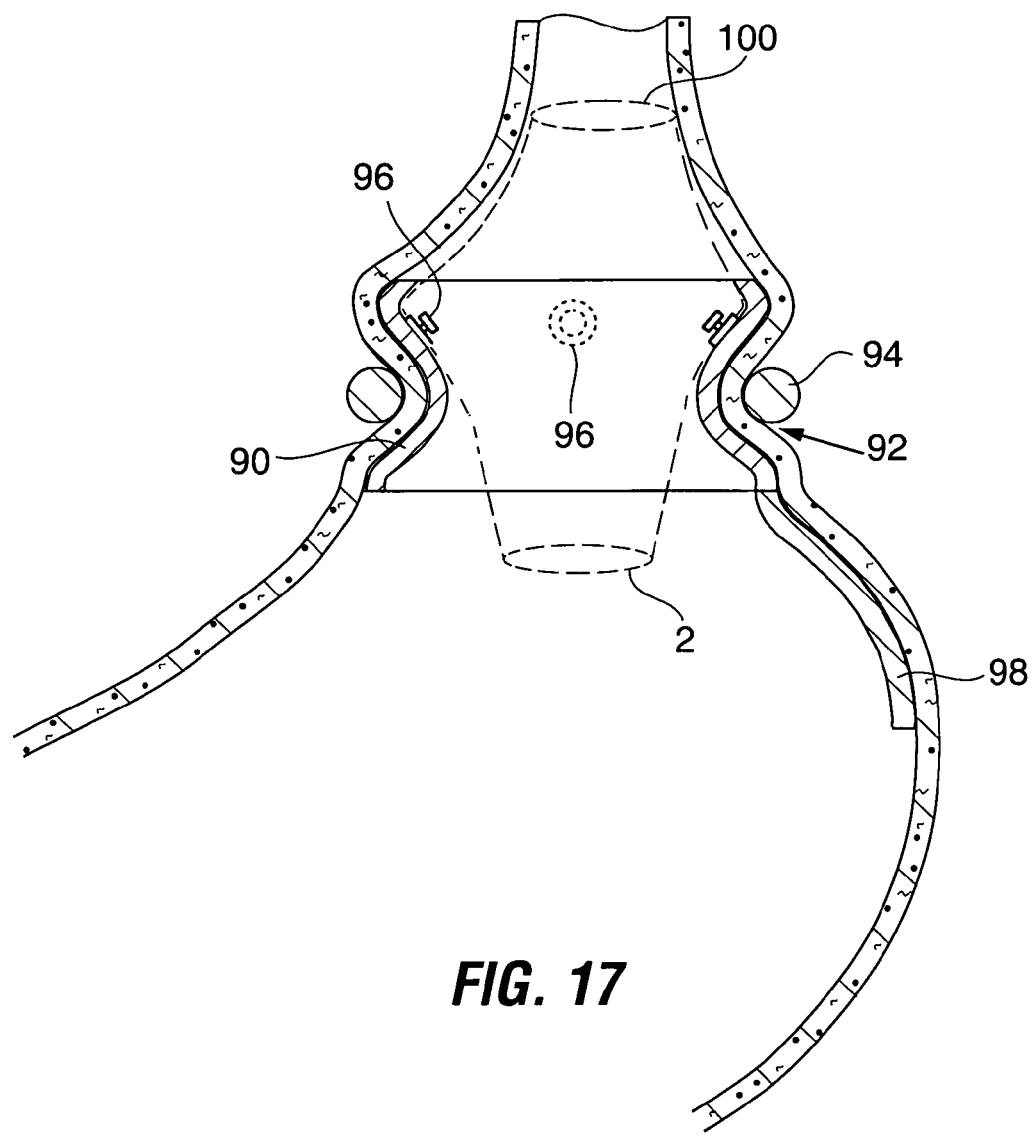
FIGS. 17-19 are cross-sectional plan views of a portion of a stomach and esophagus, showing restrictive devices and arrangements of components for retaining the restrictive devices in position.

The configuration shown in FIG. 17 is advantageous in that it can be used without sutures or other physical attachments between the implant or body tissue, although it can also be used with partial thickness sutures or anchors (which only go through a portion of the wall thickness) or "full thickness" sutures or anchors that penetrate through the full thickness of the wall of the gastro-esophageal junction, esophagus, or stomach.

Referring to FIG. 17, components positionable within the stomach include a hourglass shaped liner 90 having a waist section 92, and an implant such as pouch 2 positioned within the liner 90. Preferably, the contour of the liner 90 silhouettes that of the proximal portion of the pouch 2 as shown. The liner 90 is sufficiently rigid to restrict movement of the pouch 2 up or down within the stomach.

A ring 94 is positioned on the exterior surface of the body wall surrounding the waist portion 92 of the hourglass liner 90, such that it causes the body wall tissue to conform to the hourglass shape of the liner 90, altering the shape of the stomach by creating a stricture as shown. If necessary, the ring 94 may be secured in place using partial or full thickness sutures, barbs, clips etc. The ring 94 may have features similar to the collar 56 described in connection with FIG. 31G below.

The relative positions of the ring 94, liner 90 and pouch 2 are such that the ring holds the liner 90 in position, and the liner in turn holds pouch 2 in position. Optional mounting studs 96 may be connected to the pouch 2 and sutured through the liner 90 to the body wall using partial or full thickness sutures. Further details of studs of this type are described in connection with FIGS. 29A-29F. The liner 90 protects the mucosal lining of the stomach against erosion, and both the liner 90 and the ring 94 are themselves sufficiently flexible to prevent/minimize tissue erosion caused by their own surfaces.

An optional feature in the FIG. 17 configuration includes a fundal component 98 extending in a distal direction from the liner 90. The fundal component 98 functions to reduce the area of the fundus exposed to ingested food. Over time, the presence of the fundal component may cause cells within the stomach to decrease their production of Ghrelin, the hormone that causes feelings of hunger. Thus, the overall level of hunger experienced by a patient will decrease and may result in weight loss by the patient. Contact between the fundal component and surrounding tissue may additionally aid in weight loss by causing the patient to experience sensations of fullness.

Another optional feature in the FIG. 17 configuration includes a proximal chute 100, which extends the pouch 2 into the esophagus. This restricts dilatation of the stomach in the region above the ring 94 and thus provides additional restriction against overeating by the patient.

Figure 18:
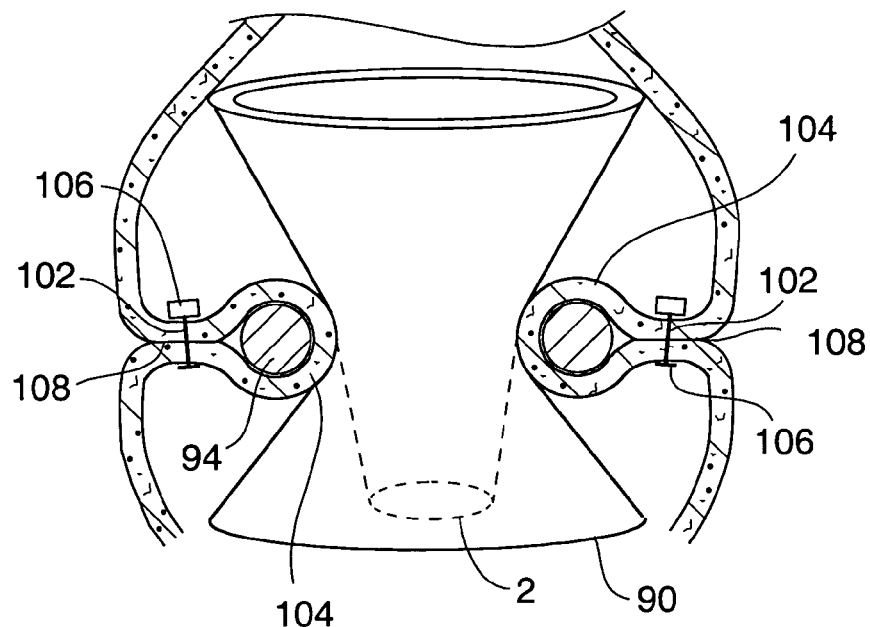

Another configuration shown in FIG. 18 is similar to the FIG. 17 configuration, but it adds sutures 102 extending between tissue above and below the ring 94 to form plications 104 in the tissue to retain the ring in place. The plications 104 are formed by grasping tissue above and below the ring, and then suturing the grasped bunches of tissue together (see FIGS. 12A and 12B and associated discussion). Obviously, in this and each of the described embodiments staples or clips may be used in place of the sutures. Pledgets or anchors 106, which may be of a type described below, may be attached to the free ends of the sutures to prevent them from sliding through the tissue. Over time, the serosal and/or mucosal tissue layers contacting one another as a result of the plications will adhere together at regions labeled 108 and thereby increase the strength of the plications. Tissue shaving, abrasion, ablation etc. of the type described above may additional be used to ensure optimal tissue adhesion. This embodiment may be varied by eliminating the ring 94, and by simply using the plications to create the narrowing in the stomach that retains the hourglass liner 90 and the pouch 2.

Figure 19:
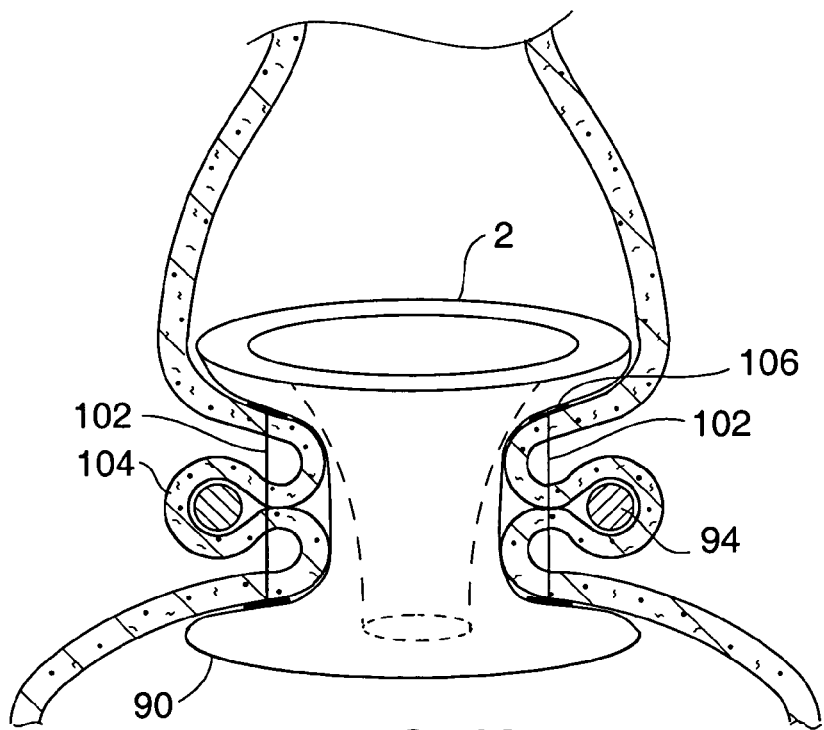

FIG. 19 shows a variation of the FIG. 18 configuration in which all components may be implanted endoscopically, thereby eliminating the need for a laparoscopic or surgical step. In the FIG. 19 embodiment, the ring 94 is positioned within the stomach, surrounding the hourglass liner 90 and pouch 2 as shown. Plications 104 are formed using sutures 102 (or clips, staples, etc.) applied from within the stomach to retain the ring 94 as shown. In the FIGS. 18 and 19 embodiments, bioabsorbable sutures may be used such that once adhesion occurs across the plications, the sutures may be absorbed by the body, leaving the ring 94 captured by the body tissue alone. Although in each of the FIG. 17-FIG. 19 configurations the ring 94 may be proportioned to affect stomach function or eating behavior, it may be desirable to proportion the ring 94 to have no such effect, so that when the pouch 2 is removed by the physician, the ring 94 may be left in place without interfering with normal eating by the patient.

Figure 20A:
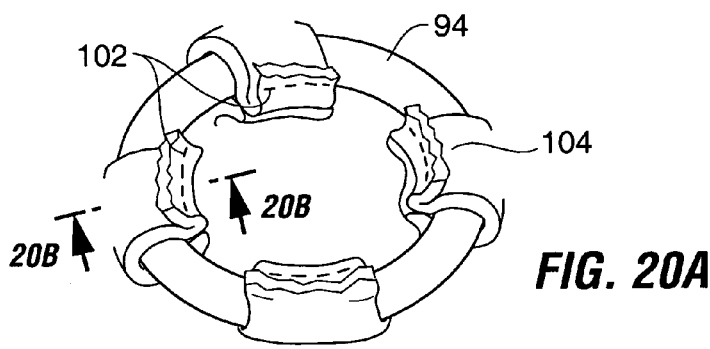
FIG. 20A is a top perspective view looking down into a stomach and illustrating the use of plications for retaining a ring within the stomach.
Figure 20B:
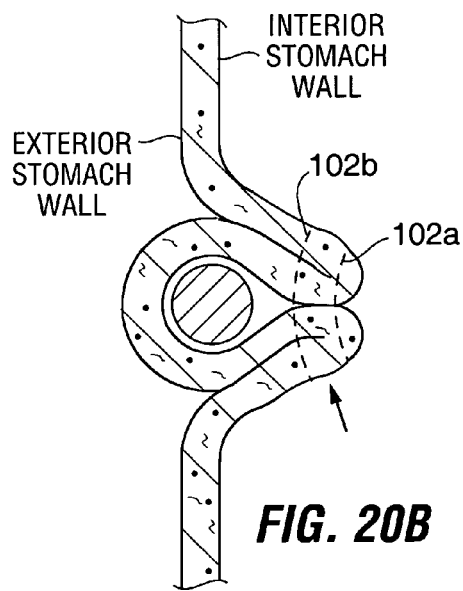
FIG. 20B is a cross-section view of a plication and ring taken along the plane designated 20B-20B in FIG. 20A.
Figure 20C:
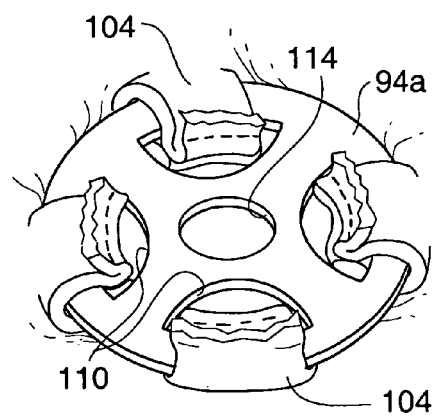
FIG. 20C is a top perspective view similar to FIG. 20A illustrating the use of plications for retaining an alternative ring within the stomach.
Figure 20D:
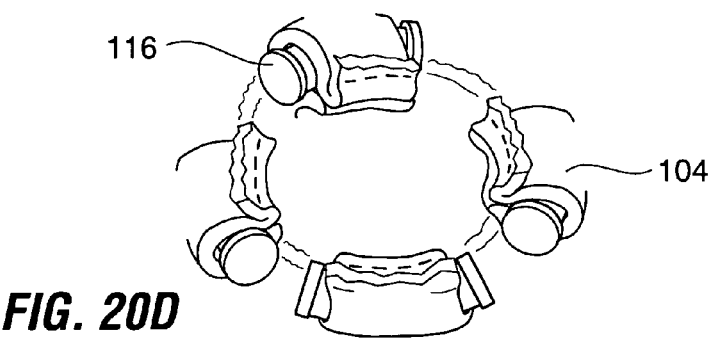
FIG. 20D is a top perspective view looking down into a stomach and illustrating the use of plications for retaining multiple members within the stomach.

FIG. 20A is a top perspective view looking down into a stomach. The figure shows plications 104 used to retain the ring 94. The plications 104 may be spaced apart around the circumference of the ring 94 as shown. FIG. 20B illustrates that the sutures may be passed through only the interior mucosal layer of tissue as indicated by suture line 102*a*, or through the interior mucosal and exterior serosal layers of tissue as indicated by suture line 102*b*.

As discussed in connection with FIGS. 18 and 19, the ring 94 may be used to "shape" the stomach in order to restrain a restrictive device and/or associated component (e.g. liner 90) against migration within the stomach. As another example shown in FIG. 20C, the ring 94*a* may be more disk-like and include windows 110 for receiving the plication tissue as well as an integral or detachable restrictive orifice 114. Preferably, the exterior perimeter of the ring seals against the surrounding tissue sufficiently to prevent passage of large amounts of food between the perimeter and adjacent tissue.

The ring 94 may also function as an anchor to which the implant may be attached using sutures, clips etc. In yet another alternative shown in FIG. 20D, bars 116 (or hooks, individual rings, hooks, buttons, barbs etc.) may be supported using tissue plications 104 and a restrictive device may be mounted to them during the same or a subsequent procedure. Because each of these embodiments relies primarily on tissue plications to support the implant, reliance on sutures or clips to connect the implant to the tissue may be minimized or even eliminated. This may in turn increase the amount of time that the implant will remain in place within the stomach.

Figure 21A:
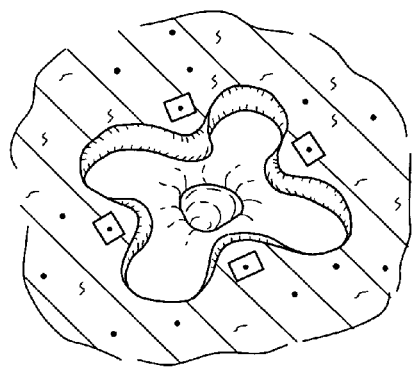
FIG. 21A is a cross-sectional top view of a stomach, illustrating plications formed in the stomach.
Figure 21B:
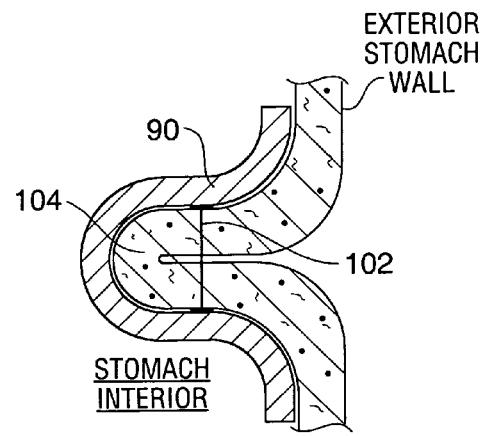
FIG. 21B is a cross-sectional elevation view of a plication illustrating use of the plications to support a liner within the stomach.

FIGS. 21A and 21B illustrate that a plication 104 may be formed without a ring, bar or other component simply by forming a fold in the tissue and passing a suture 102 through the fold. Pledgets 118 may be connected to the ends of the suture 102 to prevent it from slipping out of the tissue. The plications 104 may be used to "shape" the stomach to support the liner 90 as shown, such as in an arrangement similar to those shown in FIGS. 18 and 19.

Figure 22A:
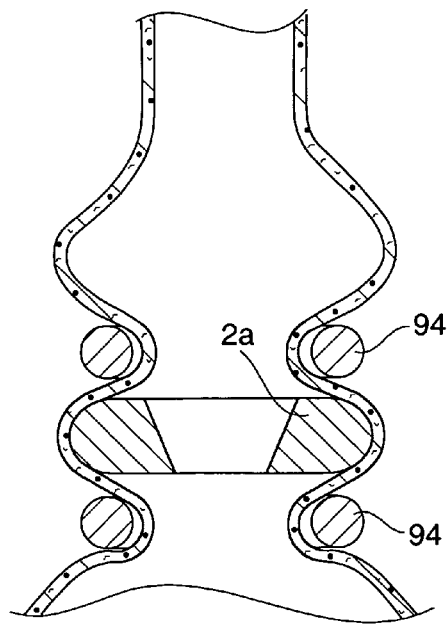
FIGS. 22A-24 are cross-sectional front views of an esophagus and stomach illustrating the use of rings to shape the stomach wall for retaining an implant.

FIGS. 22A through 24 show additional arrangements in which a ring or band may be used to facilitate retention of an implant. In the arrangement of FIG. 22A, rings 94 or restrictive bands are positioned above and below an implant 2a to provide "stops" that prevent proximal and distal movement of the device within the stomach. A similar configuration using only a ring 94 below the implant 2b is shown in FIG. 22B. As a third alternative, the rings 94 may be eliminated and plications may instead be formed in tissue above and below (or only below) the implant to prevent its migration.

Figure 23:
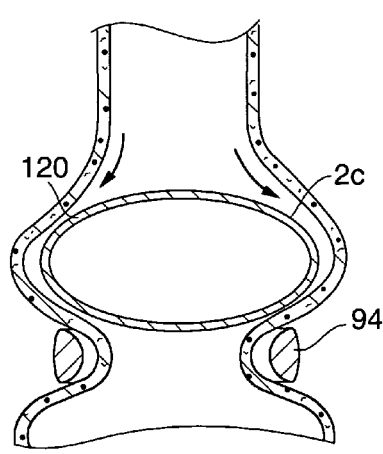

In FIG. 23, a ring 94 or band is again positioned below the implant to create a stop against distal migration of the implant. In this configuration, the implant 2c may take the form of an inflatable or self-expanding balloon 120 that is free floating in the region above the ring 94. The balloon 120 occupies a large percentage of the gastro-esophageal junction region and thus restricts food intake by only allowing food to pass through the spaces between the balloon and the surrounding body wall as indicated by arrows.

Figure 22B:
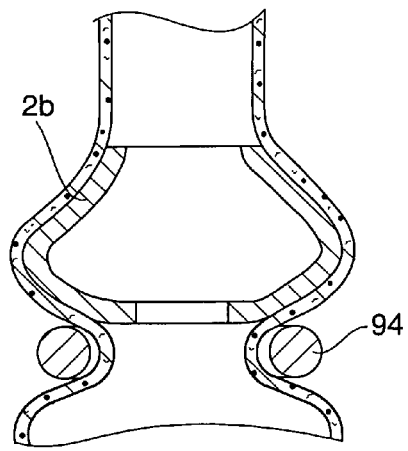
Figure 24:
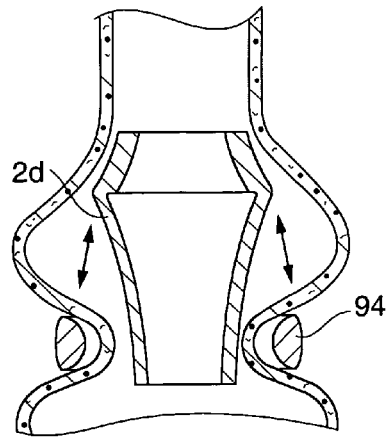

FIG. 24 shows another variation of the FIG. 22B embodiment in which the ring 94 includes magnetic elements that are of the same polarity as magnet elements in the proximal portion of the implant 2d. Thus, repulsive forces between the implant 2d and the ring 94 prevent distal movement of the implant 2d.

Figure 25:
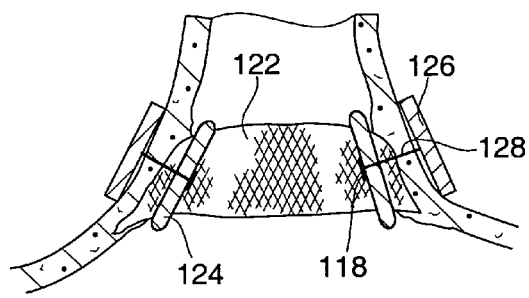
FIG. 25 is a cross-sectional front view of a proximal stomach illustrating a method of forming an anchoring structure within the stomach.

FIG. 25 shows an arrangement of components intended to form a framework within the stomach that an implant device may later be attached to. The components include a mesh band 122 positionable around the interior wall of the stomach. Interior pledgets 124 are spaced apart along the interior wall of the mesh band 122. Exterior pledgets 126 are spaced apart along the exterior wall of the stomach. The pledgets 124, 126 are connected to the mesh band by sutures 128. Over time, the mesh band will migrate into the wall tissue. Exterior pledgets 126 prevent the mesh band from migrating completely through the wall tissue, while the interior pledgets 124 prevent the mesh band from moving inwardly and separating from the wall tissue in the stomach interior. Eventually, the mesh band will become encapsulated within the wall tissue and form a sturdy structure to which implants such as pouch 2 may be attached using sutures, clips or other devices.

Figure 34A:
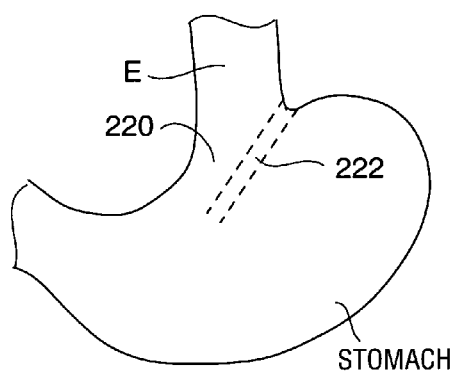
FIG. 34A is a side elevation view of a stomach which has been re-shaped to include a tunnel.
Figure 34B:
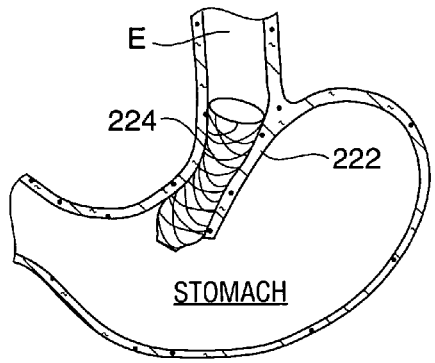
FIG. 34B is a cross-section view of the stomach showing a restrictive device anchored in the tunnel.
Figure 35A:
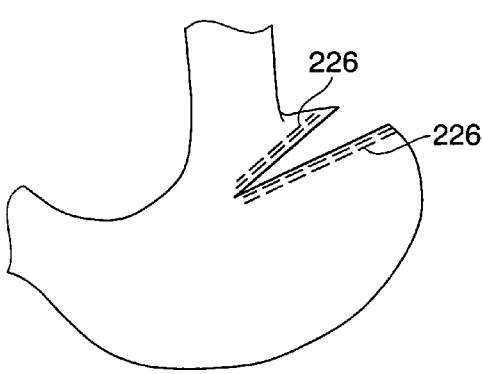
FIG. 35A is a cross-section view of a stomach which has been re-shaped for retention of an implant.
Figure 35B:
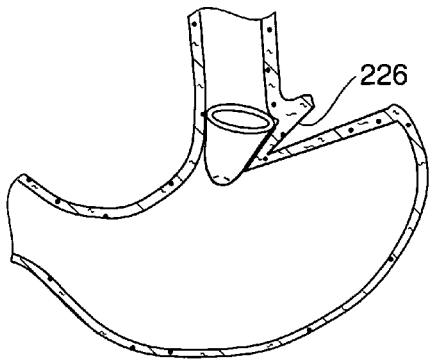
FIGS. 35B and 35C illustrate implants retained by the re-shaped wall of the stomach.
Figure 35C:
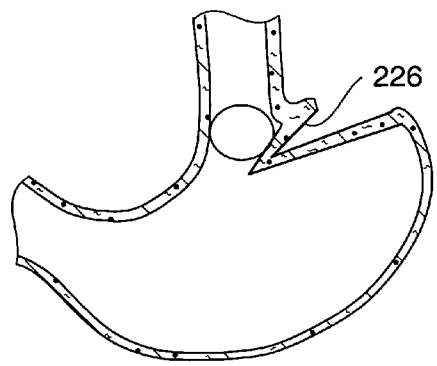

FIGS. 34A and 35A illustrate embodiments in which the stomach wall tissue may be re-shaped to allow an implant to seat against the re-shaped tissue. As shown in FIG. 34A, the stomach wall may be re-shaped to create a tunnel 220 extending from the esophagus E into the stomach S. The tunnel 220 may be formed endoscopically or surgically by suturing/stapling tissue along line 222. As illustrated in FIG. 34A, a restrictive device 224 may include an expandable stent-like structure positionable within the tissue tunnel 220 formed from re-shaped wall tissue.

Referring to FIG. 35A, an alternative re-shaping method may including forming one or more suture/staple lines 226 extending into the stomach to form a location within which an implant may seat. For example, a restrictive pouch 228 or an obstructive gastric balloon 230 may be seated within the created location such that the re-shaped wall tissue prevents the implant from descending into the intestinal tract. In the FIGS. 34A and 35A embodiments, the tissue surfaces along the suture/staple lines will eventually adhere together. If desired, the orientation of the suture/staple lines may be selected such that while the re-shaped tissue provides a platform for supporting an implant that causes a patient to eat less, removing the implant will allow the person to eat without experiencing restriction caused by the re-shaped tissue.

Figure 36B:
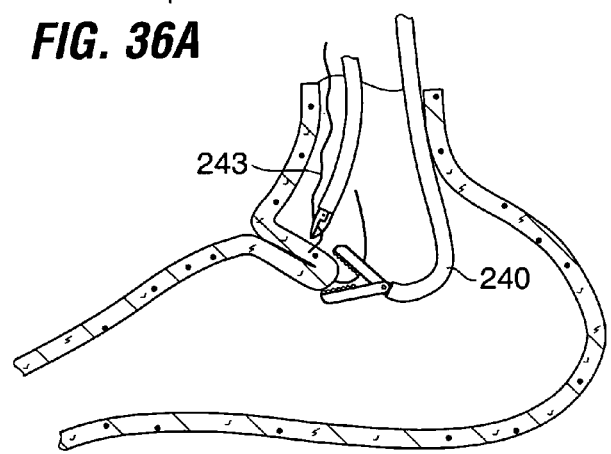
Figure 36C:
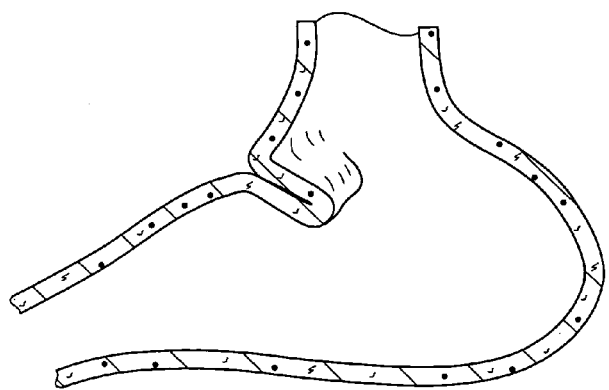
Figure 36D:
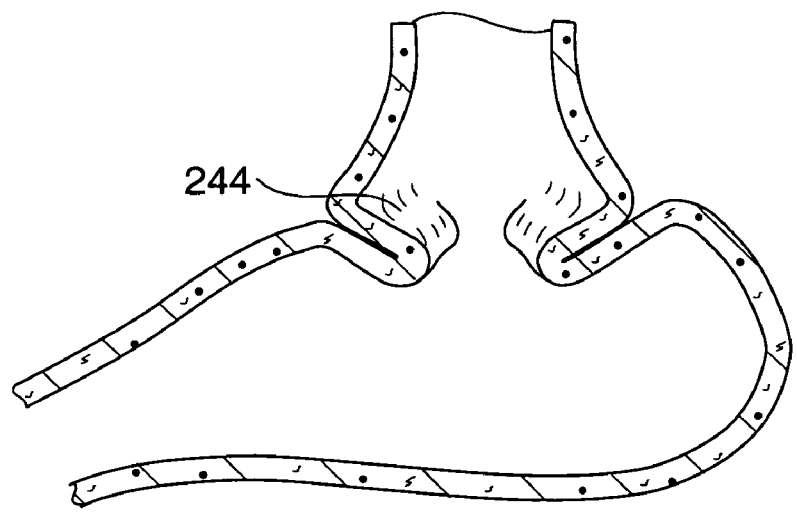
Figure 36E:
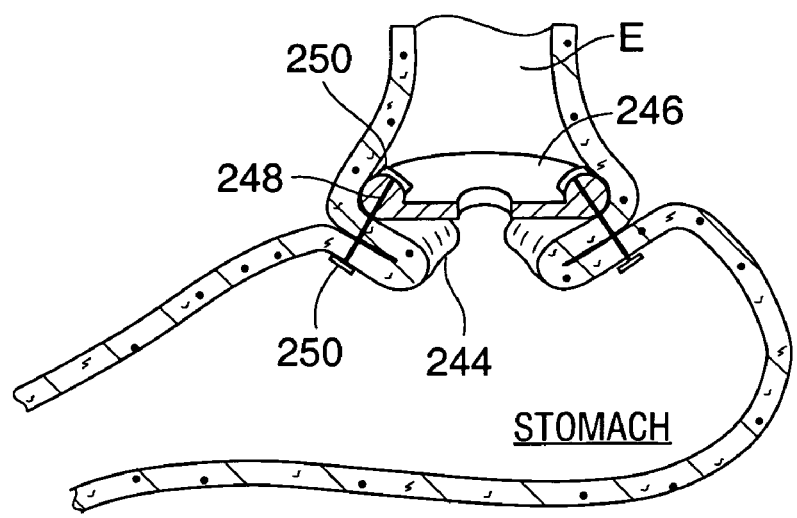

FIGS. 36A through 36F illustrate another method in which the stomach wall may be re-shaped for retention of an implant. According to this method, a circumferential ridge of tissue may be formed around the interior stomach wall, such as at the gastro-esophageal junction region, and the circumferential ridge may be used to retain the implant. Referring to FIG. 36B, a serosal plication may be formed by engaging a region of the interior stomach wall using an endoscopic grasper 240, hook, pronged instrument, or similar device. By pulling the engaged wall region inwardly, sections of external serosal tissue are drawn into contact with one another to form serosa-to-serosal plication 242 (FIG. 36D). With the plication engaged by the endoscopic instrument, a suture 243, staple or other fastener is passed through the plication 242 as shown in FIG. 36B to retain the plication. A plurality of the plications 242 are formed around the interior circumference of the stomach, thus creating a circumferential ridge 244 (FIG. 36E) of plicated tissue encircling the wall of the stomach. Over time, the opposed serosal layers form an adhesion. A restrictive implant 246 is then positioned in the stomach, proximally of the ridge 244 as shown in FIG. 36F.

In one embodiment, the circumferential ridge may function as a physical barrier that prevents migration of the implant away from the proximal stomach, similar to the manner in which the wall re-shaped by ring 94 in FIG. 22B prevents migration. Alternatively, the implant may be physically connected to the ridge 244 using sutures 248, staples or clips as shown in FIG. 36F. This may be performed by grasping the ridge 244 using an endoscopic instrument and drawing the ridge 244 in the direction of the esophagus, advancing the implant 246 into contact with the ridge 244 while retaining the ridge with the endoscopic instrument, and passing sutures/staples etc. through the implant and the ridge 244. Pledgets 250 may be used as shown in order to distribute forces over a larger surface area as described elsewhere in this application.

Attachment of the implant 246 may be performed during the same procedure in which the circumferential ridge is formed, or at a later date to permit the adhesions to form before the ridge is subjected to the stresses that will be imparted against it by the implant.

FIGS. 37A through 37D illustrate a slightly modified method for using serosal-to-serosal plication of wall tissue to form a circumferential ridge, and for securing an implant to the ridge. Referring to FIGS. 37A and 37B, tissue is plicated using an endoscopic instrument 240a which includes prong members 241. To form a plication, prong members 241 are used to pull stomach wall tissue in a proximal direction while a suture needle 243 or other fastening instrument advanced distally to drive sutures, t-bars, rivets or other fasteners downwardly into the plicated tissue as shown in FIG. 37B. Force dissipating elements such as pledgets may be used to dissipate forces against the tissue surface.

Referring to FIG. 37C, a few (for example two to four) such plications are formed around the wall to form circumferential ridge 244a (FIG. 37C).

Introduction of an implant may be performed immediately following formation of the plications, or at a later date after the opposed serosal tissue has adhered as described above. In one method of introducing the implant, a plurality of wires 252 having hooked distal ends are passed through a sheath 254 and used to hook the circumferential ridge 244a. Implant 246a, which has a plurality of small holes (not shown), is slipped over the wires by telescoping each of the small holes over a corresponding one of the wires 252. The implant 246a is compressed and passed into the sheath 254, and is then advanced through the sheath into contact with the ridge 244a while tension is maintained on the wires 252. The implant 246a may be physically connected to the ridge 244a using sutures, t-bars, or other fasteners as described in connection with FIG. 36F. This step may be performed with continued application of tension on the wires 252. As shown in FIG. 37D, a portion of the implant 246a is thus left seated against the ridge as shown in FIG. 37D.

Although various types of implants may be retained using this method as well as the other methods described in this application, the implant 246a is shown in FIG. 37D as a ring 247 that may be similar to ring 18a found on implant 10a of FIG. 4A. As with the other embodiments that utilize rings, the ring may itself function as a restrictive device, or a restrictive device may be used in combination with the ring. For example, a restrictive device may be attached to, hung from, seated against, or inserted into the ring 247.

Ring 247 may be formed of any of the materials described above in connection with pouch 2, including silicone, polyurethane, or one of a variety of types of polymers. A reinforcing element formed of an annular band of stainless steel, polymer, shape memory materials such as nitinol, shape memory alloys, or shape memory polymers may extend through the ring 247. The ring may be constructed so as to be self-expanding, so that it will spring radially open into an expanded condition upon ejection from a deployment sheath. Alternatively, the ring may be inflatable using an inflation medium such as a gas or liquid (e.g. saline), or using a photochemically or thermally curable polymer. As another alternative, the ring may be formed of a material that will degrade or erode within the body over a period of time.

The ring 247 may include an apron 256 having an annular groove 258 as shown in FIG. 37E. Various materials may be used for the ring, including PET, nylon or any of the other materials described herein. A restrictive insert 260, which may have properties similar to pouch 2 described above, is insertable into the ring 247 as shown. The restrictive insert 260 has a restrictive opening proportioned to slow the rate at which food passes through the insert and into the stomach. A selection of restrictive inserts may be provided, thus giving the physician a choice as to how much restriction should be used for a particular patient.

Insert 260 includes a rim 262 that may be snapped into groove 258 to engage the ring and insert. FIG. 37F is a view looking down the esophagus into the stomach, showing the implant 246a positioned against the plication 244. FIG. 37G is a similar view showing the implant 246a after the insert 260 has been attached to it.

In one method of using this type of implant, the physician may implant the ring 247 and delay placement of the insert 260 until the patient has had several days to adjust to the presence of the implant. Later, the insert 260 may be endoscopically passed down the esophagus into the stomach, and be snapped into place. On a later date, the physician may choose to remove the insert 260 and replace it with a more restrictive (i.e. one having a smaller exit orifice) or a less restrictive insert (i.e. one having a large exit orifice), depending on the needs of the patient. If desired, the insert may be formed of a material that degrades or erodes after a period of time, thereby eliminating the need for removal of the insert.

External Reinforcements

Figure 2B:
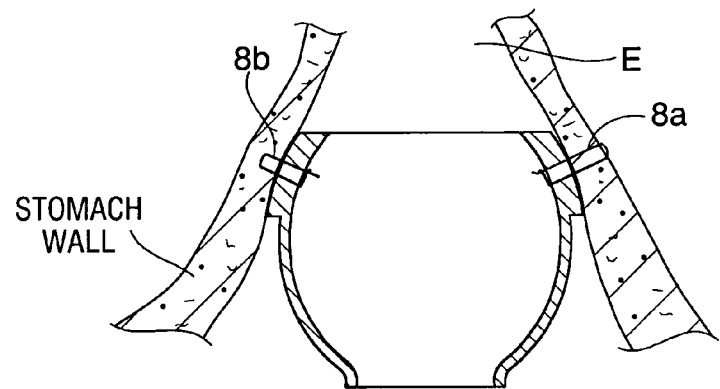
FIG. 2B is a cross-sectional elevation view of an esophagus and proximal stomach, showing the restrictive device of FIG. 2A implanted in the gastro-esophageal junction region.

Several components described in this disclosure function as external reinforcement devices. As discussed in FIG. 2B, the implant such as pouch 2 may be sutured or clipped into place by passing a full thickness suture 8a from the pouch 2 through the adjacent stomach tissue and back to the pouch. However, in some patients it may be desirable to "buttress" the sutures 8a by passing them through an external reinforcement device positioned on the exterior surface of the wall. Some of these types of reinforcing devices have been mentioned in the preceding section.

Examples of external reinforcement devices include pledgets 130 (FIG. 26A) or t-bars 132 (FIG. 26B), each of which distributes forces imparted against the suture over a larger surface area. Pledgets or t-bars may be quite large (e.g. 10-30 mm in diameter) or fairly small (e.g. 1-2 mm in diameter) as dictated by the particular application. Examples of material suitable for the pledgets or t-bars include silicone, felt, and/or the materials listed above for use in constructing the pouch. T-bars may also be formed of metallic bars crimped onto suture ends.

During implantation of the pledgets 130, the implant such as pouch 2 (FIG. 2A) may be introduced into the stomach endoscopically, while the pledgets are placed in contact with the exterior of the stomach a laparoscopic or surgical approach. Sutures are passed from within the stomach, through the stomach wall, through the pledgets, and back to the interior of the stomach. If desired, this may be carried out in two procedures: for example a first laparoscopic procedure in which pledgets are laparoscopically sewn onto the exterior wall of the stomach, and a second endoscopic procedure in which the implant is passed through the esophagus and into the stomach and in which sutures are passed between the implant, stomach wall, and pledgets.

During implantation of the t-bars, the end of the suture having the t-bar attached to it is endoscopically positioned adjacent the exterior wall of the stomach, and the free end is sewn through the stomach wall and the internally positioned implant wall.

FIG. 27A shows an alternative external reinforcement device which takes the form of a "moly bolt" type fasteners 134 that may be introduced endoscopically through the esophagus into the stomach. Referring to FIG. 27B, during implantation, the implant (e.g. pouch 2) is positioned against the stomach and fasteners 134 are passed from the interior of the implant through the implant wall and through the stomach wall. Each fastener 134 includes an internal wire or string (not shown) that is attached to its distal portion 136. The distal portions 136 of the fasteners 134 are expanded into the position shown in FIG. 27C by pulling on these wires or strings, thereby anchoring the fasteners 134 in place.

Other types of external reinforcement devices are shown in FIGS. 28A through 28C. In the FIG. 28A embodiment, inflatable balloons 138 may be passed through the implant and stomach wall from the stomach interior (in similar fashion to that shown in FIG. 27B for the moly bolt type fasteners), and then subsequently inflated such that the expanded balloons remain on the exterior surface of the stomach.

Figure 26A:
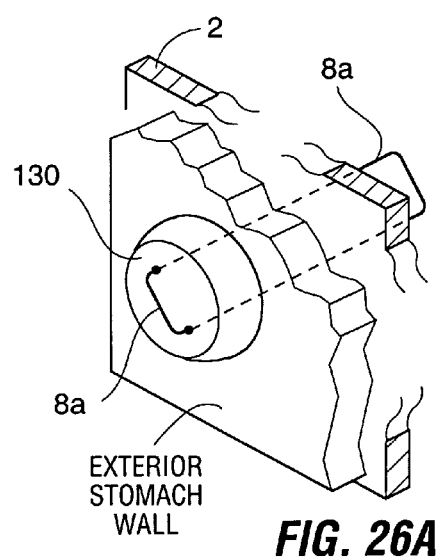
FIG. 26A is a schematic illustration of a portion of an exterior stomach wall, showing a pledget anchored to the wall as an external reinforcement to an internally positioned restrictive device.
Figure 26B:
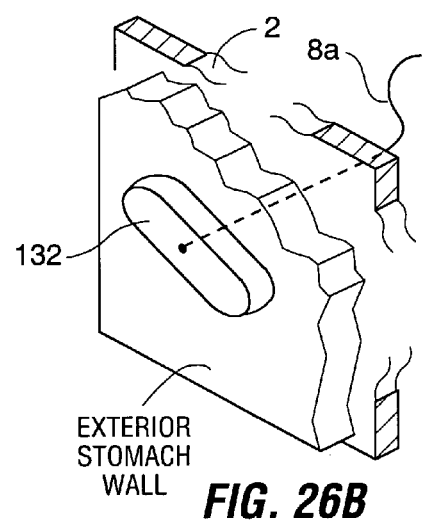
FIG. 26B is a schematic illustration similar to FIG. 26A, showing a T-bar anchored to the wall as an external reinforcement to an internally positioned restrictive device.

FIGS. 28B and 28C illustrate alternatives to the pledgets 130 described with respect to FIG. 26A. As with the FIG. 26A pledget, the pledgets of FIGS. 28B and 28C are positioned on the exterior wall of the stomach and sutures are passed through the pledgets to attach the implant to the stomach wall. As shown in FIG. 28B, the pledgets 130a may have roughened surfaces to prevent them from slipping through the suture openings in the stomach wall. FIG. 28C illustrates that pledgets 130b may be formed of mesh or other material known to promote cell ingrowth, such that over time the stomach wall tissue will grow into the pledget to enhance anchoring.

As another alternative to the pledget 130, a pledget may be formed in situ by injecting a drop of gel onto the exterior surface of the stomach, where the gel is a type that will solidify on the tissue surface. The gel may be delivered laparoscopically by approaching the stomach wall from outside the stomach, or it may be delivered endoscopically by injecting the gel using a needle passed through the wall of stomach from the stomach interior. Once the gel hardens into a pledget, the implant may be anchored to the hardened gel pledget using sutures, clips, etc. passed through the stomach wall. As yet another alternative, the gel may be injected in between the serosal and mucosal layers of stomach wall tissue to form the gel pledget within the stomach wall.

Figure 29B:
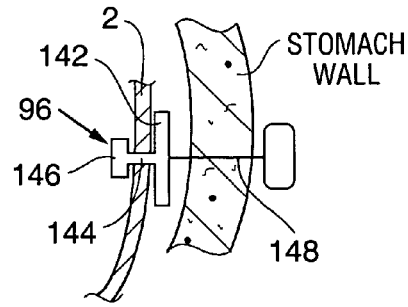
FIGS. 29B through 29F are side elevation views showing examples of means for connecting the device of FIG. 29A through stomach tissue to the externally positioned external reinforcement device. The stomach tissue is shown in cross-section.

Naturally, each of the external reinforcement devices described above must in some way be connected to the implant located in the interior of the stomach. FIG. 29A shows a "stud" type fastener 96 of a type that may be attached to a implant within the stomach, and that is also connected to an external reinforcement device (not shown in FIG. 29A). Fastener 96 includes a first button 142 having a pin 144, and second button 146 having a bore for receiving the pin 144. As shown in FIG. 29B, pin 144 is passed through the wall of the implant (e.g. pouch 2) such that one of the buttons 142 is on the exterior of the implant and the other button 146 is on the exterior of the pouch. Fastener 96 is then connected to an external reinforcement device such as a pledget 130 positioned on the exterior wall of the stomach as shown.

As shown in FIGS. 29B through 31F, various devices may be used to connect the fastener 96 to the pledget 130. It should be noted that although the implant is only shown in FIG. 29B, it should be assumed that in FIGS. 29C through 29F implant is attached to the fastener such as in the manner shown in FIG. 29B.

Figure 29C:
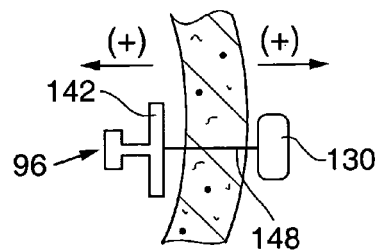
Figure 29D:
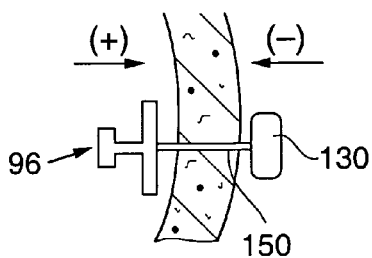
Figure 29E:
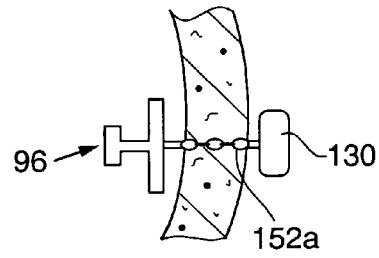
Figure 29F:
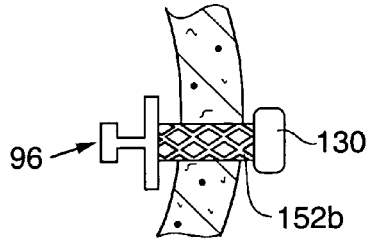

Referring to FIG. 29B, a suture 148 may be sewn through the stomach wall and attached to both the fastener 96 and the pledget 130 using suitable means. For example, to secure the suture 148 to the fastener 96, the suture may be tied to the pin 144, or it may be threaded through an opening in the button 142 and into a bore in the pin 144, and the pin 144 may be crimped down to secure the suture within it. A variety of types of sutures may be used for this purpose, for example monofilament, braided suture, cotton, silk, or bioabsorbable suture. The length of suture between the fastener 96 and pledget 130 may be highly tensioned or loosely tensioned. Referring to FIG. 29C, if it is desirable to keep the suture in tension, the pledget 130 and fastener 96 may be magnetized to the same polarities such that they will resist movement towards one another as indicated by arrows and to thus maintain the tension of the suture. Alternatively, as shown in FIG. 29D the pledget 130 and fastener 96 may be magnetized to opposite polarities such that the attraction between them holds both the pledget, implant, and fastener against the stomach tissue. This embodiment may utilize a rigid post 150 (e.g. stainless steel, nitinol, plastic) extending between the pledget 130 and fastener 96 to protect the tissue from being compressed between the pledget 130 and fastener 96. As another alternative, the rigid post 150 may provide the connection between the pledget 130 and fastener 96, without the use of magnetism. As shown in FIGS. 29E and 29F, a physical connector between the pledget 130 and fastener 96 may be formed of a material that promotes tissue ingrowth, such as a chain 152a or mesh 152b formed of nitinol, stainless steel, polymer, or bio-absorbable material.

Figure 30A:
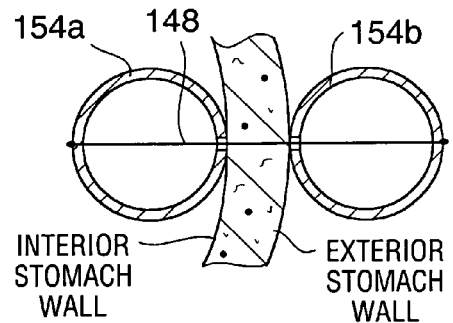
FIGS. 30A and 30B are cross-sectional side elevation views showing self-balancing external reinforcements connected to stomach tissue.
Figure 30B:
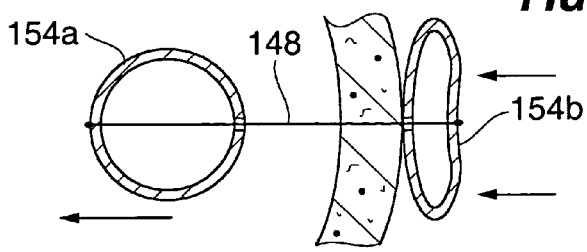

Referring to FIG. 30A, external reinforcement may alternatively be provided by a combination of self-balancing anchors. This may take the form of a pair of balloon pledgets 154a, 154b connected by a suture 148 extending through the stomach wall such that one balloon 154a is within the stomach and the other balloon 154b is outside the stomach. The suture preferably extends through the interior of each balloon and is attached to the balloon at a point that is furthest from the adjacent stomach wall. The implant (not shown) is connected to the suture adjacent to the balloon 154a positioned within the stomach. As illustrated in FIG. 30B, the balloons are proportioned such that when force draws one of the balloons 154a away from the stomach wall (such as when the implant pulls inwardly in response to food pressure) the other balloon compresses and flattens against the wall, thereby increasing the effective pledget size and thus distributing the force over a larger area. It should be noted that the balloon pledgets could be replaced with other resilient structures such as three-dimensional mesh, stent-like frame structures, deformable elastomers, or other structures that will deform when subjected to force but that will resume their original shape upon release of the force.

Collars

Another form of external reinforcement device is an external collar encircling the exterior of the stomach. FIGS. 31A through 31I show a variety of collar configurations. Some of these configurations are intended to be physically connected to the implant using sutures or other connection methods, including those shown in FIGS. 29B-29F for connecting the implant to the pledget-type devices. These connections may be made with or without the stud fasteners of FIG. 29A. When connected to the implant, the collars may function like the pledgets 130 to facilitate even distribution of forces around the implant. The collars and pledgets may also be combined such that a collar encircles the exterior stomach wall and pledgets on the exterior surface of the collar are connected to the device using sutures passed through the collar and the stomach wall. In this configuration, the collar aids in force distribution and also prevents the pledgets from eroding the stomach wall.

For other configurations, the collar is not physically connected to the implant, but may be positioned to restrict movement of the device.

The collar embodiments of FIG. 31A through 31F are designed to have the implant device anchored to them at anchor points 156. The collars are intended to be flexible so as to more evenly distribute forces rather than to have significant forces build at any one anchor point. In the FIG. 31A embodiment, the flexibility of the collar 158 comes from its pleated structure. The implant 2 within the stomach is attached to the collar at 158 anchoring points 156. The FIG. 31B collar 160 is formed of a coil spring. In both of these embodiments, the flexibility of the collar allows the anchoring points 156 to move with the stomach rather than allowing forces at the anchor points to build when such stomach movement occurs.

Figure 31A:
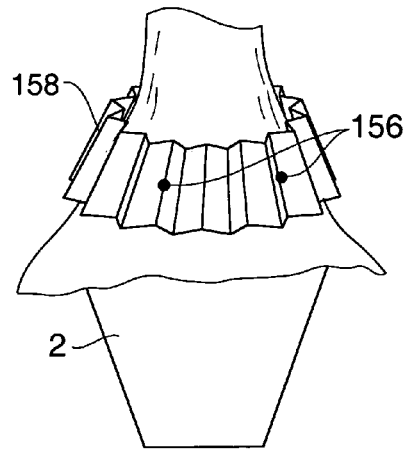
FIGS. 31A through 31I are schematic illustrations of a lower esophagus and proximal stomach, each showing a different embodiment of an external collar.
Figure 31B:
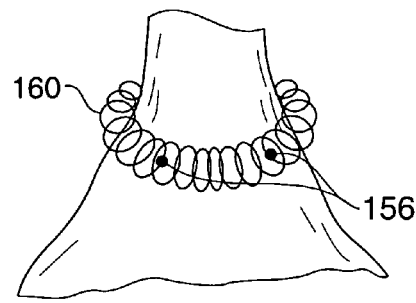
Figure 31C:
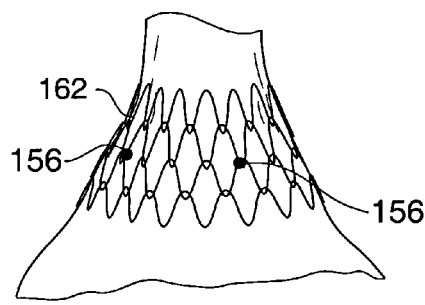
Figure 31D:
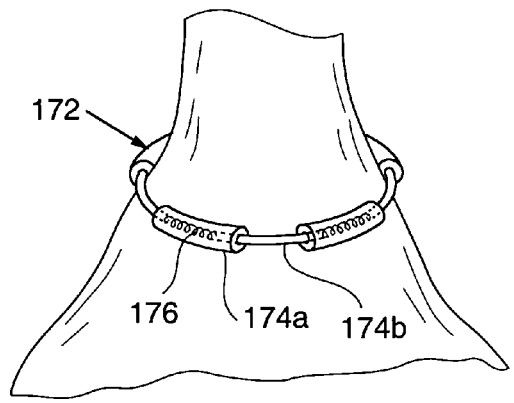
Figure 31E:
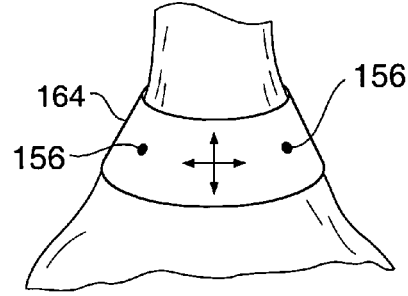
Figure 31F:
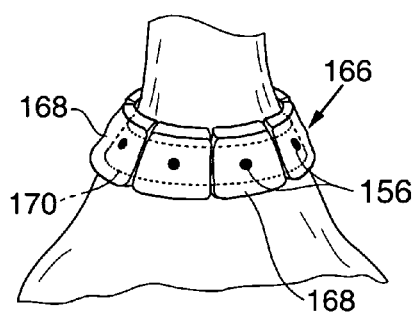

Similar properties are found in the FIG. 31C-31E embodiments. In the FIG. 31C embodiment, the collar 162 is formed of material such as stainless steel, polymeric, or nitinol mesh that has flexibility in multiple directions. The FIG. 31E collar 164 is also capable of stretching in multiple direction due to its use of a thin flexible polymeric sheet. In the FIG. 31F embodiment, the collar 166 includes a plurality of individual pledgets 168 mounted to an elastic member 170. FIG. 31D shows an expandable collar 172 formed of telescoping components 174a, 174b. Spring members 176 connect the components 174a, allowing the collar to expand and contract with the stomach.

Figure 31G:
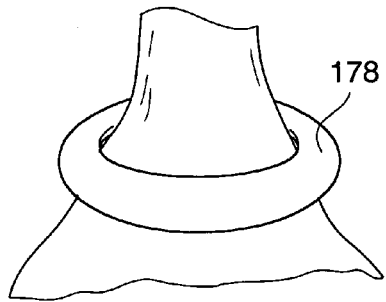
Figure 31H:
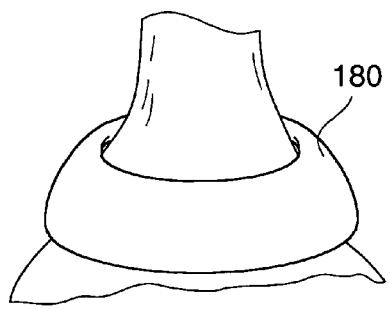
Figure 31I:
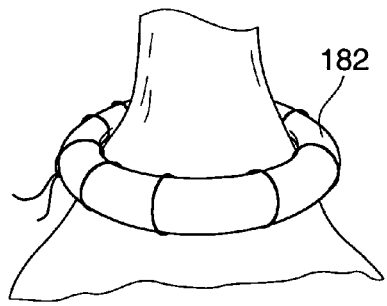

Referring to FIGS. 31G, 31H and 31I, the collar may be a simple round or oval-shaped ring. It may have a torroidal shape like the collar 178 of FIG. 31G, or a tapered shape like the collar 180 of FIG. 31H which conforms to the tapered shape of the exterior stomach wall. The collar may be rigid or flexible. Alternatively, referring to FIG. 31I, collar 182 may be flexible but include a tensioning cable that may be activated to increase the rigidity of the collar. With these embodiments, sutures attached to the implant may be sewn through the stomach wall and be attached to the collar, or the collar may remain physically separate from the implant but function to maintain the implant's position as discussed in greater detail in connection with FIG. 17.

Figure 32A:
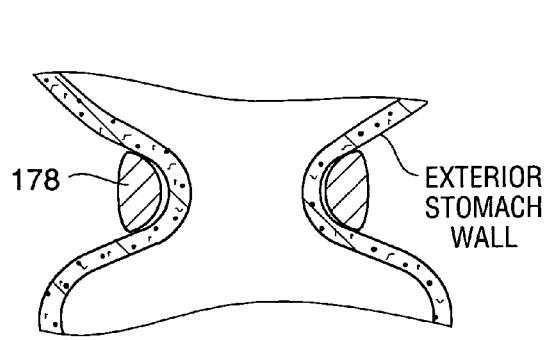
FIG. 32A is a cross-sectional side elevation view of a distal esophagus, proximal stomach, and external collar.

FIG. 32A shows a front cross-section view of the collar 178 surrounding an exterior stomach wall. As shown, collar 178 may have a D-shaped cross-section to minimize tissue trauma.

Figure 32B:
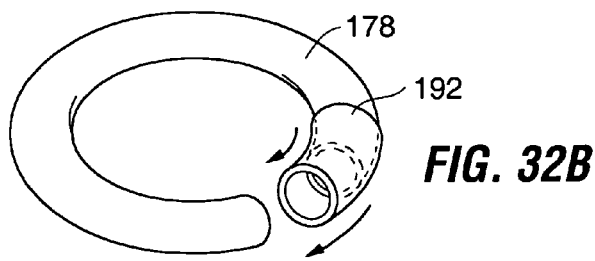
FIG. 32B is a perspective view of the collar shown in FIG. 32A in a straightened configuration.

Because the collar is intended to be wrapped around the stomach, its design must be such that it can be introduced into the stomach cavity in an elongate configuration, and then have its free ends attached to form it into a loop around the stomach. As illustrated in FIG. 32B, collar 178 may include a slot 184 at one end and a tab 186 at the opposite end. Tab 186 is engageable within the slot to form the collar in to a loop. Raised buttons 188 on the tab 186 may snap into recesses 190 in the slot to lock the collar in the closed loop. The size of the collar may be pre-selected by cutting the tab 186 to the desired length before it is inserted into the slot.

Figure 32C:
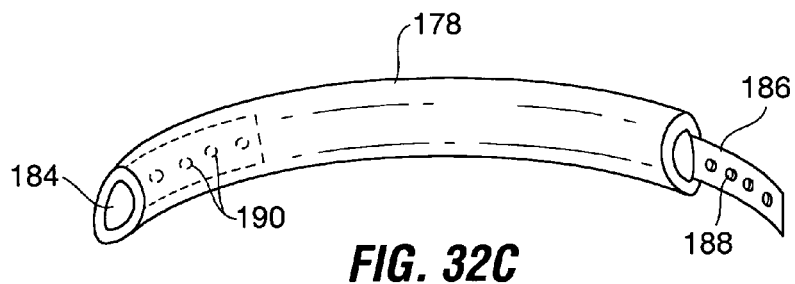
FIG. 32C is a perspective view of a collar of the type shown in FIG. 32B, but having an alternative locking mechanism.
Figure 33A:
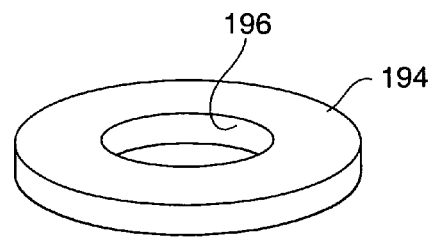
FIG. 33A is a perspective view of an example of an alternative restrictive device, in which the restrictive device takes the form of a rigid ring.
Figure 33B:
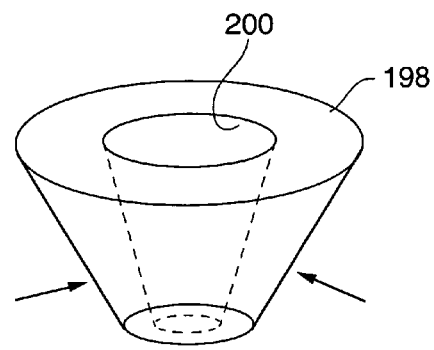
FIG. 33B is a perspective view of another example of an alternative restrictive device, which has a tapered geometry.
Figure 33C:
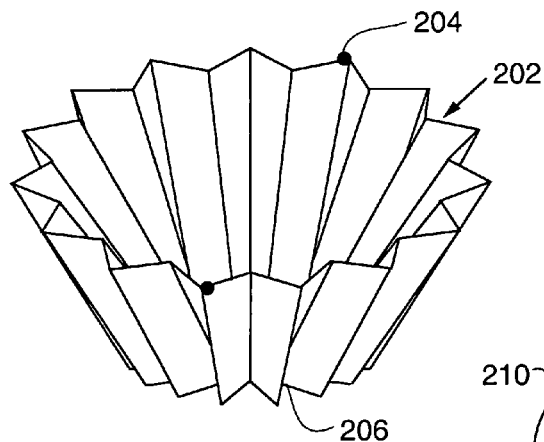
FIG. 33C is a perspective view of still another example of an alternative restrictive device, which has a bellows configuration.
Figure 33D:
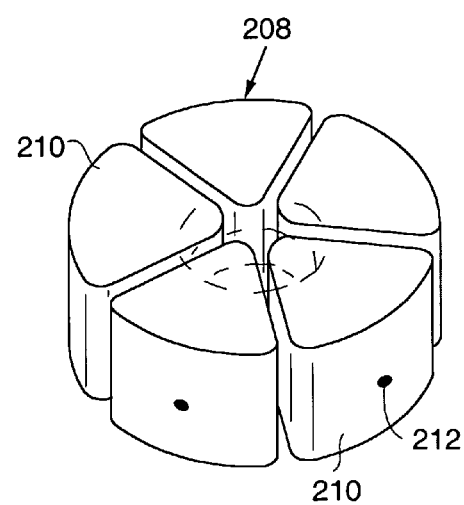
FIG. 33D is a perspective view of another example of an alternative restrictive device, which includes a collection of separate segments that collectively form a restriction in the stomach.

As an alternative shown in FIG. 32C, collar 178 may include a sleeve 192 that is slidable over the collar as indicated by arrows to retain the ends of the collar 178 together once the collar has been positioned around the stomach.

Alternative Restrictive Devices

The flexible nature of the pouch 2 allows it to move in response to stomach movement, thereby producing little or no stress on the sutures or anchors holding the pouch in place. This is believed desirable towards minimizing the chance that the implant will detach from the stomach wall. Other restrictive devices and methods of retaining them are shown in FIGS. 20C, 22A, 22B, 23 and 24.

FIGS. 32A through 32D show restrictive devices having alternative features which may likewise minimize risk for detachment. These devices may be used with or without the various attachment devices described in this application.

FIG. 32A shows a rigid ring 194 positionable in the gastro-esophageal junction region and attached using sutures or other means similar to those described for pouch 2. The ring 194 may be flexible for endoscopic insertion, and then convertable (e.g. by inflation to a high pressure using a detachable inflation tube) to a rigid ring following implantation so as to restrict movement of the stomach. Such restriction of stomach movement is intended to minimize stresses on the sutures or anchors and thus reduce the risk of detachment.

Ring 194 includes a flow-restrictive orifice 196 through which food passes. If desired, the ring 194 may include a circumferential region surround the orifice 196 that is independently inflatable or deflatable to adjust the diameter of the exit orifice.

FIG. 32B shows an alternative restrictive device 198 which has a tapered configuration, such that forces imparted against the device by the stomach (as indicated by arrows) as well as forces imparted by food passing through the tapered passageway 200 in the device 198 will cause the device to seat more tightly within the gastro-esophageal junction region. As with the other embodiments, sutures, anchors, clips, adhesives etc. may be used to attach the device 198 to the stomach walls.

FIG. 32C shows a restrictive device 202 that is pleated between anchor points 204. The pleats allow the device 202 to expand in response to forces against it, and thus minimize stress at the anchor points. As with the other restrictive devices, device 202 includes a restrictive orifice 206.

Restrictive device 208 of FIG. 32D is formed of a plurality of individual members 210, each of which is separately attachable to the tissue of the gastro-esophageal junction using sutures, clips or the like at anchoring points 212. The individual members 210 collectively form a restriction at the gastro-esophageal junction so as to minimize food intake by the patient. The amount of restriction may be reduced by reducing the size of the members 210. Because the individual members 210 are physically separate from one another, movement of the stomach will produce little or no stress on the anchors.

Tissue Modification to Increase Tissue Strength

If desired, the tissue of the stomach, esophagus, or gastro-esophageal junction may be treated using techniques such as mechanical abrasion, RF ablation/coagulation, laser ablation, or chemical abrasion that can strengthen the tissue such as by forming a layer of scar tissue. Cyanoacrylate coatings or growth inhibitors may also be applied to the tissue to strengthen it. These forms of tissue modification may be used in embodiments in which implant devices are physically connected to the tissue using sutures, staples, etc, or in embodiments in which there is no such physical connection but in which increased tissue strength is desired for prevention of erosion.

Reinforcement of Tissue Adhesions

Figure 38:
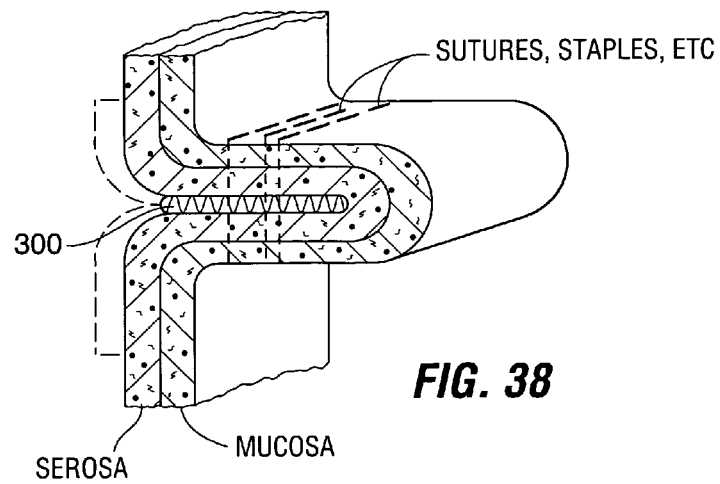
FIG. 38 illustrates a plication using a reinforcing patch between the tissue layers.

Many of the embodiments described above rely upon formation of tissue adhesions between opposed tissue layers. Referring to FIG. 38, a reinforcing patch 300 may be positioned between the tissue layers (e.g. serosal layers as shown, or alternatively mucosal layers). The patch may function as a scaffolding that promotes tissue ingrowth and/or function to reinforce the adhesions that form.

The patch may be a synthetic or non-synthetic mesh, porous material, slotted material, or any other material through which adhesions will form or onto which tissue will grow. Examples include, but are not limited to, polypropylene, materials sold under the trade names Goretex or Dacron, or tissue graft material such as the Surgisis material sold by Wilson Cook Medical, Inc. The material may be treated with tissue-ingrowth promoting substances such as biologics. Sutures (which may be bioabsorbable), pledgets, t-bars or other fastening means are used to hold the tissue layers together at least until adhesions bond the tissue layers together. Eventually, adhesions form between the tissue layers (and through and/or onto the interstices of the patch) and serve to reinforce the bond between the tissue layers. A patch of this type may be used in connection with any embodiments which create tissue adhesions between tissue layers. A few examples are illustrated in FIGS. 39A through 42B.

Figure 39A:
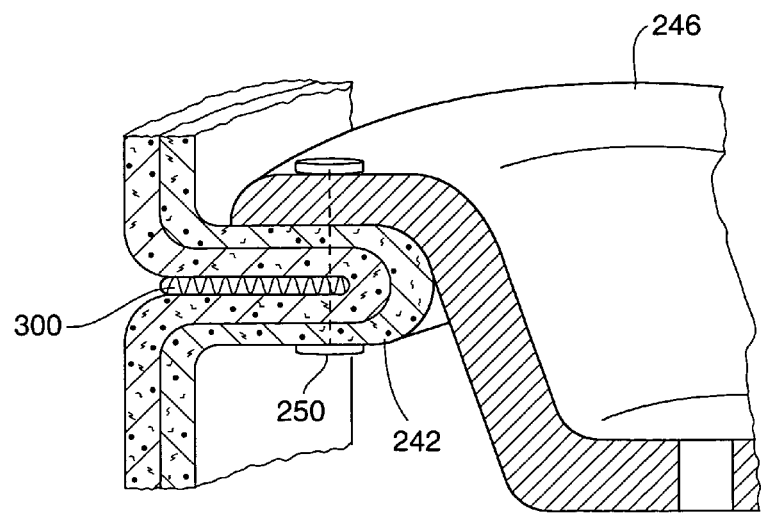
FIGS. 39A and 39B illustrate formation of plications similar to those shown in FIG. 36F but using a reinforcing patch between the tissue layers.
Figure 39B:
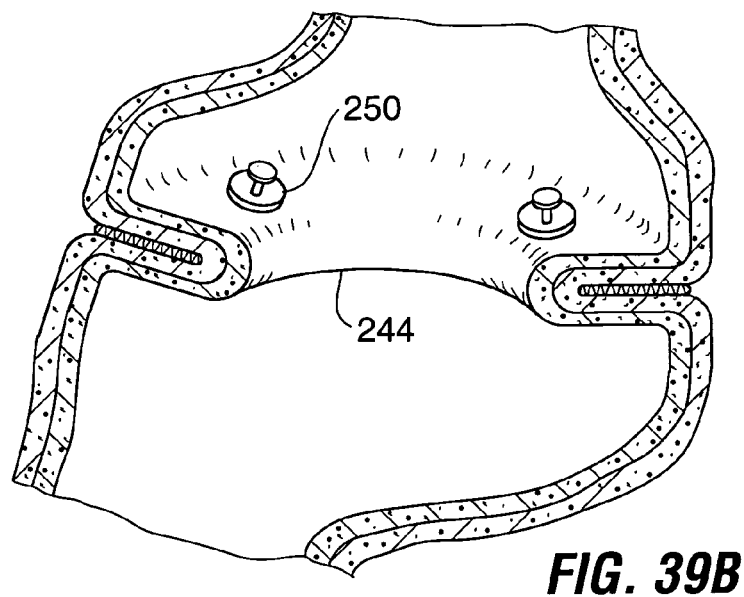

FIGS. 39A and 39B illustrate an embodiment similar to the FIG. 36F embodiment in which serosal plications 242 are formed to create a circumferential ridge 244 and in which a restrictive implant 246 is attached to the ridge 244 or seats against the ridge without a physical connection. The FIG. 39A/B embodiment differs, however, in that patch 300 is positioned between the serosal layers. Anchoring studs or pledgets 250 may be passed through the serosal tissue layers and the patch 300 as shown to secure the plication and (if desired) to serve as an attachment point for an implant such as a restrictive device.

Figure 40:
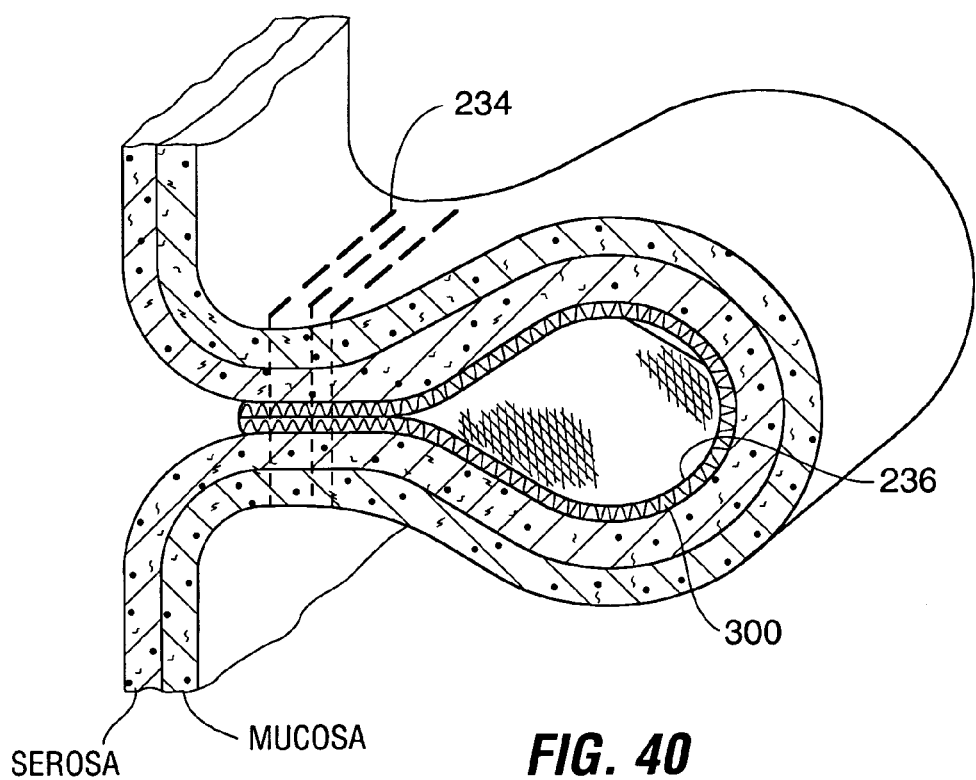
FIG. 40 illustrates the use of a reinforcing patch in a tissue pocket similar to the tissue pocket of FIG. 12E.

FIG. 40 illustrates an embodiment similar to FIG. 12E in which a pocket 236 is formed using a serosal to serosal connection, but which has been modified to include patch 300 between the serosal tissue layers. Patch 300 may be formed of a strip of material formed into a loop, such that it lines a portion of the pocket 236 as shown, thereby protecting the lined portion of the pocket against friction imparted by a device element (not shown) positioned within the pocket 236. As an alternative shown in FIG. 41A, a plication of the type shown in FIG. 38 is formed, and a cut 302 is then formed to remove the innermost portion of the tissue fold. Patch 300 is formed into a loop and anchored in place between the serosal layers forming the plication, with the loop extending into the stomach as shown. Using this configuration, a device element may be positioned within the loop formed by the patch.

Figure 41A:
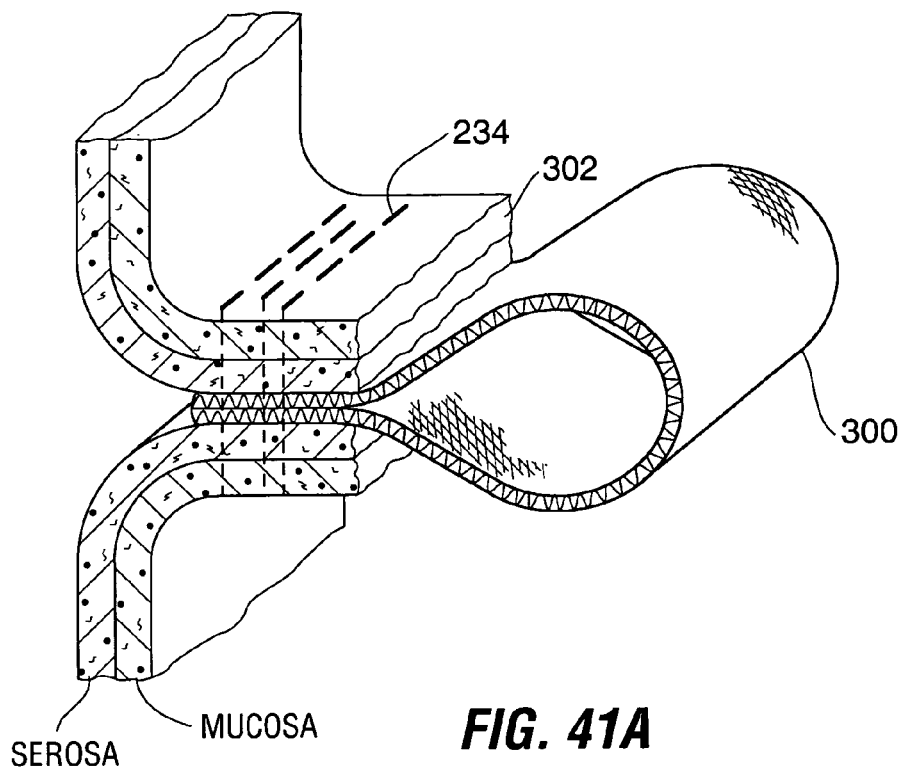
FIGS. 41A and 41B illustrate alternative uses of reinforcing patches for reinforcement of plications and for use in retaining restrictive device.
Figure 41B:
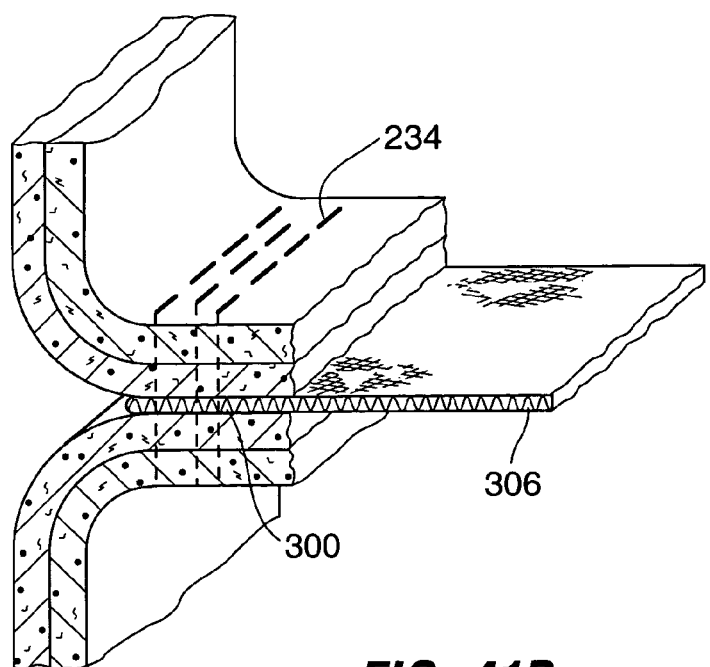

In an alternative to the embodiment of FIG. 41A, patch 300 may include an extension 306 in place of the loop 300. A restrictive device (not shown) may be attached to the extension 306 using sutures or other fasteners, or the restrictive device may simply seat against the extension without being physically attached to it. Although the extension 306 is shown as a mesh element, it should be appreciated that the extension need not be formed of the same material as the patch. Instead, it may have any type of material and shape (e.g. a hook) to which the restrictive device may be coupled or against which the restrictive device may be seated. As yet another alternative, one or more extensions 306 may be configured to obstruct passage of food into the stomach and thus themselves function as the obesity-controlling device without the addition of a separate device.

Figure 42A:
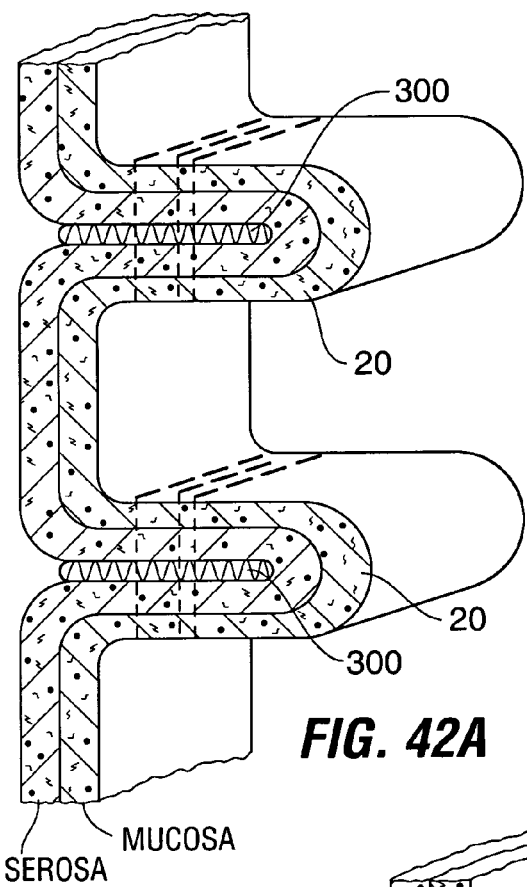
FIGS. 42A and 42B illustrate a method similar to the method described in connection with FIG. 8C, but adding the use of a reinforcing patch.
Figure 42B:
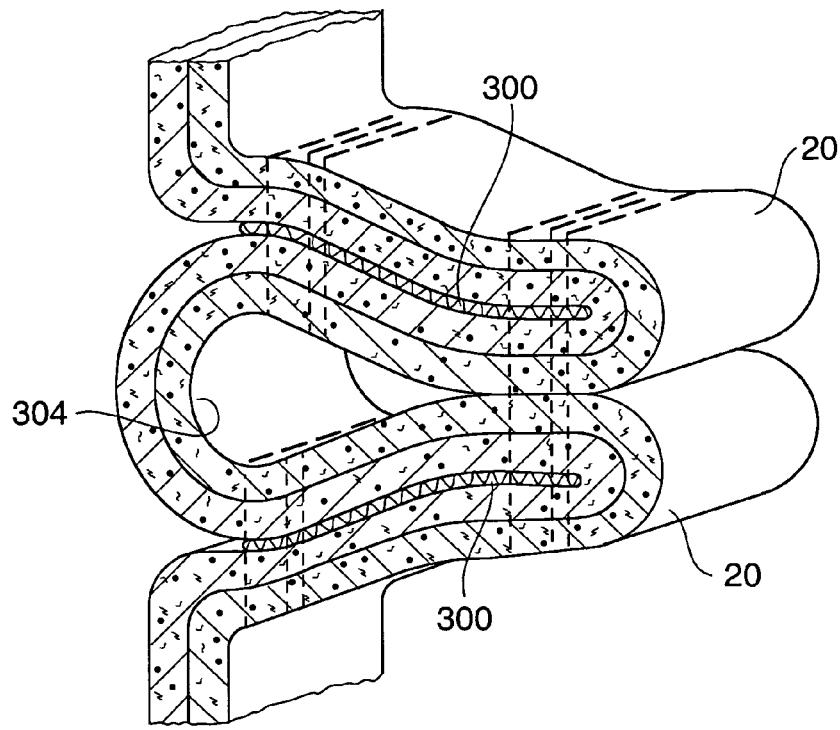

An embodiment similar to that shown in FIG. 8C is illustrated in FIGS. 42A and 42B. Here a pair of serosal plications are formed, each with a patch 300 between the serosal layers. The folds 20 of the two plications are connected to one another as shown in FIG. 42B to form a pocket 304 between the plications. The ends of the folds 20 may be cut prior to attachment as described with respect to FIGS. 8C and 8D, or they may be left uncut. Additionally, another patch may be positioned between the folds to reinforce the adhesions that will ultimately grow between them.

Various components and methods have been described herein. These embodiments are given by way of example and are not intended to limit the scope of the present invention. It should be appreciated, moreover, that the various features of the embodiments that have been described may be combined in various ways to produce numerous additional embodiments. Also, while various materials, dimensions, shapes, implantation locations, etc. have been described for use with disclosed embodiments, others besides those disclosed may be utilized without exceeding the scope of the invention. For example, the retention methods and devices are not limited to use within the gastro-intestinal system and may be used for implants placed elsewhere in the body.

We claim:

1. A method of forming a plication in stomach tissue, comprising the steps of:
    positioning a patch between a first serosal tissue surface and a second serosal tissue surface;
    forming a tissue structure on the stomach wall, the tissue structure having an interior space bounded by tissue and at least one opening extending into the interior space, the step of forming the tissue structure including fastening the first and second serosal tissue surfaces with the patch therebetween, such that a first face of the patch contacts the first serosal tissue surface and a second face of the patch contacts the second serosal tissue surface; and
    causing an adhesion to form through the patch between the first and second serosal tissue layers.

2. The method of claim 1, wherein the tissue structure forms a pocket between a portion of the tissue layers, and wherein the method includes causing a portion of the patch to line the pocket.

3. The method of claim 1, wherein the method is further for positioning an implant within the stomach, and wherein the method includes the step of positioning at least a portion of an implant in the interior of the tissue structure.

4. The method of claim 1, wherein the method includes causing the adhesion to form at least partially through the patch.

5. The method of claim 1, wherein the method includes causing at least a portion of the adhesion to extend through the patch from the first serosal tissue surface to the second serosal tissue surface.

6. The method of claim 1 wherein the patch includes openings, and wherein at least a portion of the adhesion extends into openings in the patch.

7. The method of claim 6, wherein the patch is formed of mesh or fabric and wherein the openings include interstices of the mesh or fabric.

8. The method of claim 6, wherein the patch is formed of porous material and wherein the openings include pores of the porous material.

9. The method of claim 6 wherein the patch is a slotted material and wherein the openings are slots in the slotted material.

10. The method of claim 1, wherein positioning the patch includes positioning the patch with the first face in contact with the first serosal tissue surface and the second face in contact with the second serosal tissue surface.

11. The method of claim 1, further including the step of attaching the layers of body tissue to retain the patch at least until the adhesion forms.

12. The method of claim 1, wherein the adhesions form a bond between the opposed layers of body tissue and wherein the patch reinforces the bond.

13. The method of claim 12, wherein the attaching step includes stapling the layers together.

14. The method of claim 12, wherein the attaching step includes suturing the layers together.

15. The method of claim 1 wherein the tissue structure forms a tunnel between a portion of the tissue layers.

16. The method of claim 1, wherein forming the tissue structure comprises attaching at least two tissue layers in apposition to form a tissue fold, and forming an opening in the tissue fold to create the interior space.

* * * * *